United States Patent
Matsuda et al.

(10) Patent No.: US 10,264,998 B2
(45) Date of Patent: Apr. 23, 2019

(54) BLOOD VESSEL IMAGING APPARATUS AND PERSONAL AUTHENTICATION SYSTEM

(71) Applicant: Hitachi, Ltd., Chiyoda-ku, Tokyo (JP)

(72) Inventors: Yusuke Matsuda, Tokyo (JP); Naoto Miura, Tokyo (JP); Akio Nagasaka, Tokyo (JP); Takafumi Miyatake, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 35 days.

(21) Appl. No.: 15/529,899

(22) PCT Filed: Nov. 28, 2014

(86) PCT No.: PCT/JP2014/081490
§ 371 (c)(1),
(2) Date: May 25, 2017

(87) PCT Pub. No.: WO2016/084214
PCT Pub. Date: Jun. 2, 2016

(65) Prior Publication Data
US 2017/0325721 A1 Nov. 16, 2017

(51) Int. Cl.
*A61B 5/00* (2006.01)
*G06K 9/00* (2006.01)
(Continued)

(52) U.S. Cl.
CPC ............ *A61B 5/117* (2013.01); *A61B 5/0059* (2013.01); *A61B 5/0064* (2013.01); *A61B 5/489* (2013.01);
(Continued)

(58) Field of Classification Search
None
See application file for complete search history.

(56) References Cited

U.S. PATENT DOCUMENTS

| 2002/0048014 A1 | 4/2002 | Kono et al. |
| 2006/0274920 A1 | 12/2006 | Tochikubo et al. |

(Continued)

FOREIGN PATENT DOCUMENTS

| JP | 2002-92616 A | 3/2002 |
| JP | 2004-331021 A | 11/2004 |

(Continued)

OTHER PUBLICATIONS

International Search Report (PCT/ISA/210) issued in PCT Application No. PCT/JP2014/081490 dated Feb. 10, 2015 with English translation (Four (4) pages).

(Continued)

*Primary Examiner* — Sumati Lefkowitz
*Assistant Examiner* — David Perlman
(74) *Attorney, Agent, or Firm* — Crowell & Moring LLP

(57) ABSTRACT

In the conventional art, there has been a problem that it is difficult to perform, with a high usability and at a high precision, authentication that accepts a wide range of variation of showing attitude of a hand or a finger and ensures obtaining a clear blood-vessel image of a finger. Provided is a blood-vessel image capturing apparatus including an opening portion formed in a surface of a housing, plural light sources disposed beside the opening portion and arranged in a lattice pattern, a sensor configured to obtain position information of a hand shown above the opening portion, a light amount control portion configured to select an irradiation light source to irradiate the hand from the plural light sources on a basis of the position information and control a light amount of the irradiation light source, and an image capturing portion configured to capture an image of a blood vessel included in a finger portion of the hand irradiated with light from the irradiation light source.

12 Claims, 33 Drawing Sheets

(51) Int. Cl.
*G06K 9/68* (2006.01)
*A61B 5/117* (2016.01)
(52) U.S. Cl.
CPC ........... G06K 9/00013 (2013.01); *G06K 9/68* (2013.01); *G06K 2009/00932* (2013.01)

(56) References Cited

U.S. PATENT DOCUMENTS

2008/0063243 A1 3/2008 Kiyomizu et al.
2012/0327227 A1* 12/2012 Ikeda .................... G01M 3/38
                                                              348/143
2014/0286541 A1 9/2014 Kiyomizu et al.

FOREIGN PATENT DOCUMENTS

| | | |
|---|---|---|
| JP | 2007-310429 A | 11/2007 |
| JP | 2008-65570 A | 3/2008 |
| JP | 2014-174644 A | 9/2014 |
| JP | 2014-183877 A | 10/2014 |
| WO | WO 2004/111940 A1 | 12/2004 |
| WO | WO 2013/093953 A1 | 6/2013 |

OTHER PUBLICATIONS

Japanese-language Written Opinion (PCT/ISA/237) issued in PCT Application No. PCT/JP2014/081490 dated Feb. 10, 2015 (Four (4) pages).

* cited by examiner

BLOOD VESSEL IMAGING APPARATUS AND PERSONAL AUTHENTICATION SYSTEM

TECHNICAL FIELD

The present invention relates to an apparatus and a system that authenticate an individual by using biological information of human.

BACKGROUND ART

In the case of using biological authentication for identity verification of persons of an unspecified number, a degree of proficiency in using an authentication apparatus varies between the persons. A user with a low degree of proficiency does not have much knowledge about a proper showing position or showing attitude of a living body. Therefore, there are some cases where the user shows the living body in an improper position or attitude and the precision of authentication decreases. Therefore, biological authentication with a high usability that is capable of performing authentication at a high precision even in the case where there is a large variation in showing positions and showing attitudes of a living body is desired.

PTL 1 describes an individual authentication apparatus and so forth that cause one finger to be shown in a predetermined showing region and control a light source for irradiation in accordance with a variation in the attitude of the finger and with a showing position of the finger.

CITATION LIST

Patent Literature

PTL 1: WO13/093953

SUMMARY OF INVENTION

Technical Problem

However, PTL 1 only addresses a variation in the attitude of the finger in a narrow area in an upper portion of a finger showing portion on the premise that one finger is shown from a predetermined angle. Therefore, the acceptable range of variation of the showing attitude of the user is restricted, and the degree of freedom in positions and attitudes of a hand is limited. Thus, there has been a problem that it is difficult to perform, with a high usability and at a high precision, authentication that accepts a wide range of variation of showing attitude of a hand or a finger and ensures obtaining a clear blood-vessel image of a finger.

Solution to Problem

An example of a means for resolving the above-described technical problem is a blood-vessel image capturing apparatus including an opening portion formed in a surface of a housing, plural light sources disposed beside the opening portion and arranged in a lattice pattern, a sensor configured to obtain position information of a hand shown above the opening portion, a light amount control portion configured to select an irradiation light source to irradiate the hand from the plural light sources on a basis of the position information and control a light amount of the irradiation light source, and an image capturing portion configured to capture an image of a blood vessel included in a finger portion of the hand irradiated with light from the irradiation light source.

Advantageous Effects of Invention

According to the configuration of the present invention, an advantageous effect that a clear blood-vessel image, for example, an image of a vein of a finger, can be obtained and individual authentication can be performed at a high precision with respect to a position variation of a hand, an attitude variation of a hand, a position variation of a finger, and an attitude variation of a finger in a predetermined three-dimensional space.

DESCRIPTION OF EMBODIMENTS

First Exemplary Embodiment

Figure 1:
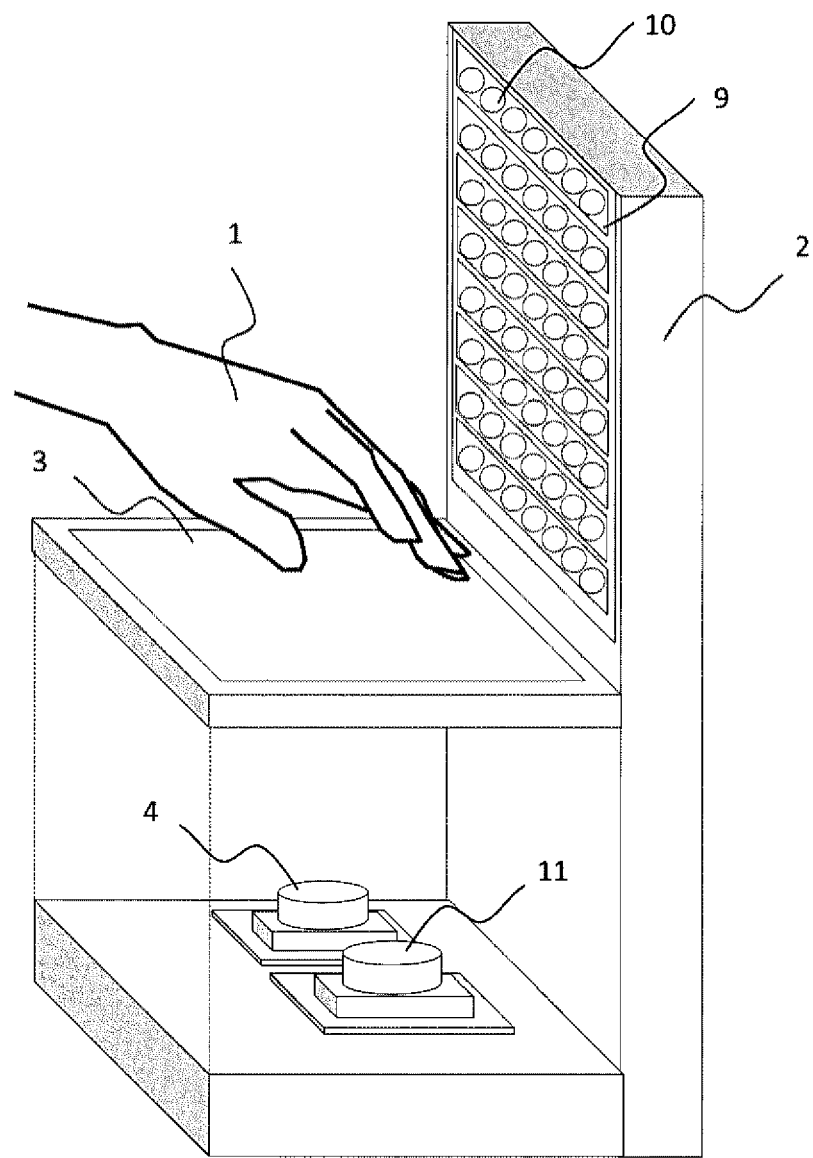
FIG. 1 is an example of an authentication apparatus that implements the present invention.
Figure 2:
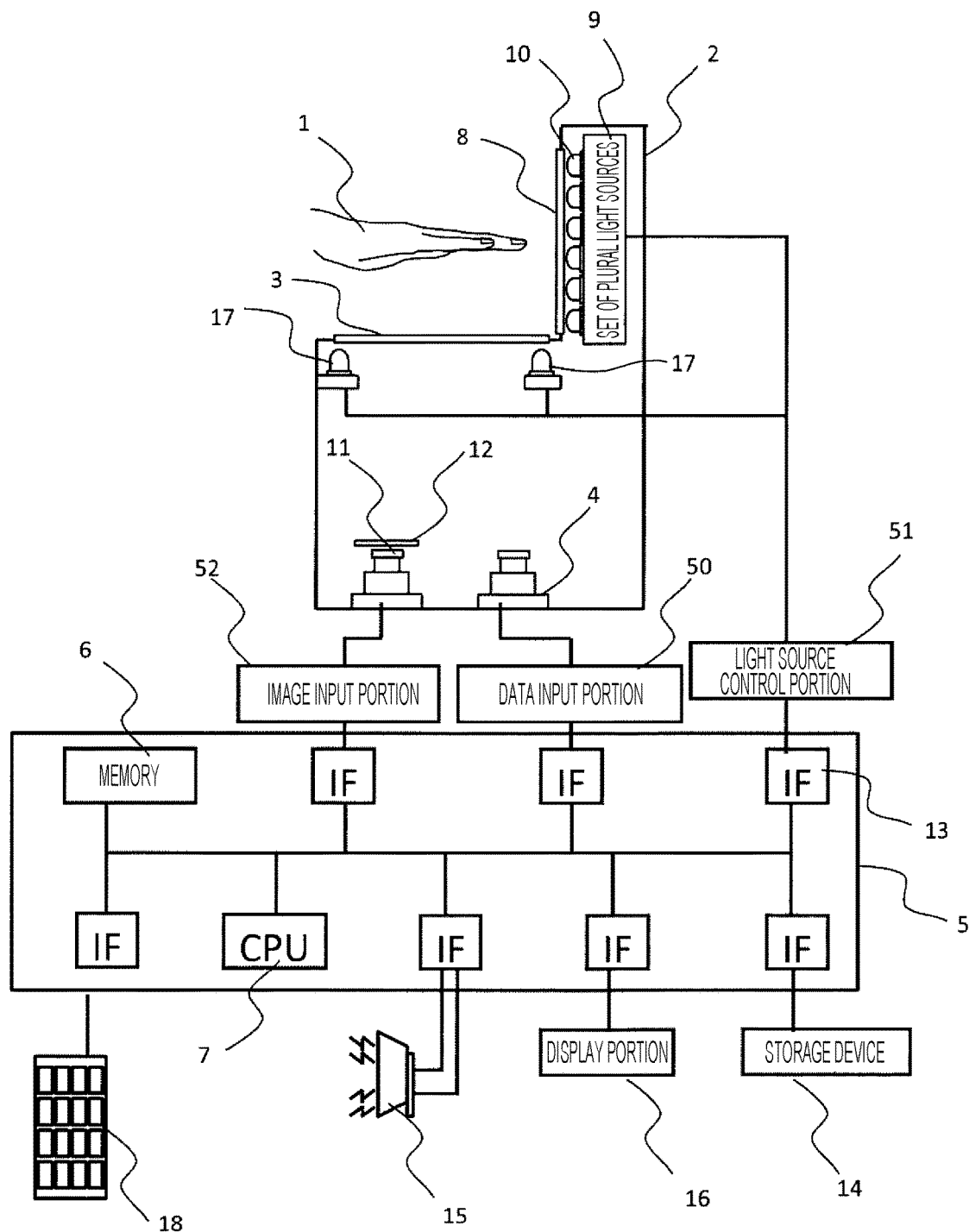
FIG. 2 is a system configuration example of the authentication apparatus that implements the present invention.

In the present exemplary embodiment, an example of a basic configuration for performing authentication by controlling a light source in accordance with the position or attitude of a shown hand to capture a clear blood-vessel image of a finger will be described. To be noted, although a case of a biological authentication apparatus that performs individual authentication in a housing will be described as an example in the present exemplary embodiment, it goes without saying that an individual authentication system that performs authentication in an authentication portion of a server or the like installed outside the housing may be configured and the housing corresponding to an authentication apparatus 2 itself may be configured as a blood-vessel image capturing apparatus that transmits information of a captured blood-vessel image to the authentication portion. FIG. 1 is an example of an authentication apparatus that implements the present invention, and FIG. 2 is a schematic diagram of a configuration of the authentication apparatus of FIG. 1. An opening portion 3 is provided on a surface of a housing of the authentication apparatus 2 such that a hand 1 can be shown above the opening portion 3 of the authentication apparatus 2 when capturing a blood-vessel image of fingers. A distance sensor 4 disposed inside a housing below the opening portion 3 converts light received for distance measurement into an electric signal and saves the electric signal in a computer 5 as distance data between the hand 1 and the distance sensor via a data input portion 50. A CPU 7 calculates the position of the hand 1, the attitude of the hand 1, the position of a finger, the attitude of the finger, and the like from the distance data saved in the computer 5 by using a program stored in a memory 6. On the basis of the calculated position or attitude of the hand 1 or the fingers, a light amount control portion 51 controls a light source array 9 disposed inside an opening portion 8, selects an irradiation light source from plural point light sources 10 constituting the light source array 9, and irradiates the fingers with irradiation light, and an image capturing portion 11 disposed below the opening portion 3 receives light that has passed through an optical filter 12. To be noted, although a single point light source 10 maybe selected as the irradiation light source, it is desirable to select plural adjacent point light sources 10 as one set in the present exemplary embodiment in view of the fact that the movement range of the hand and the image capturing range are large.

Light is converted into an electric signal by the image capturing portion 11, and the electric signal is saved in the computer 5 as an image via an image input portion 52. The saved image is once stored in the memory 6. Then, the CPU 7 performs authentication in accordance with a program stored in the memory 6 by matching one or more images stored in the memory with one or more images stored in advance in a storage device 14. Images of blood vessels of plural fingers can be captured simultaneously by irradiating the plural fingers with the irradiation light from the point light sources 10. As to calculation of the position and attitude of the hand 1, the position and attitude of the hand may be detected by using an image of the hand captured by the image capturing portion 11, and the image of the hand 1 captured by the image capturing portion 11 and the distance data between the hand 1 and the distance sensor 4 may be both used. A user may be notified of an authentication result through sound by using a loudspeaker 15, and, similarly, the user may be also notified of the authentication result by displaying the authentication result on a display portion 16. A user can be notified of a state of authentication processing by providing visible light sources 17 at the opening portion 3, detecting a shown hand in a stand-by state, and causing the visible light sources to emit light of a different color for each case of authentication in progress, successful authentication, and failed authentication. In addition, authentication (1:1 authentication) can be performed by showing the hand after specifying a registered person by inputting a personal identification number or an ID via a keyboard 18.

A transparent material such as acrylic resin or glass may be used for the opening portion 3 and an opening portion 25. The apparatus can be configured such that the user cannot see the inside of the apparatus by attaching films that cut visible light and pass only near infrared light to the opening portion 3 and the opening portion 25.

The light source array 9 is disposed beside the opening portion 3 or 25. By disposing the light source array 9 beside the opening portion 3 or 25, in particular, in front of the user showing the hand, it becomes possible to form an open space in a moving direction and in an upward direction when, for example, performing authentication while the user is moving as will be described later, and thus it becomes possible to improve usability for the user.

In the light source array 9, plural light sources are arranged in a lattice pattern. In other words, the plural light sources are arranged such that multiple light sources are arranged in both of a direction in which an opening plane of the opening portion 3 is formed and an upward direction with respect to a surface on which the apparatus is placed.

Figure 3:
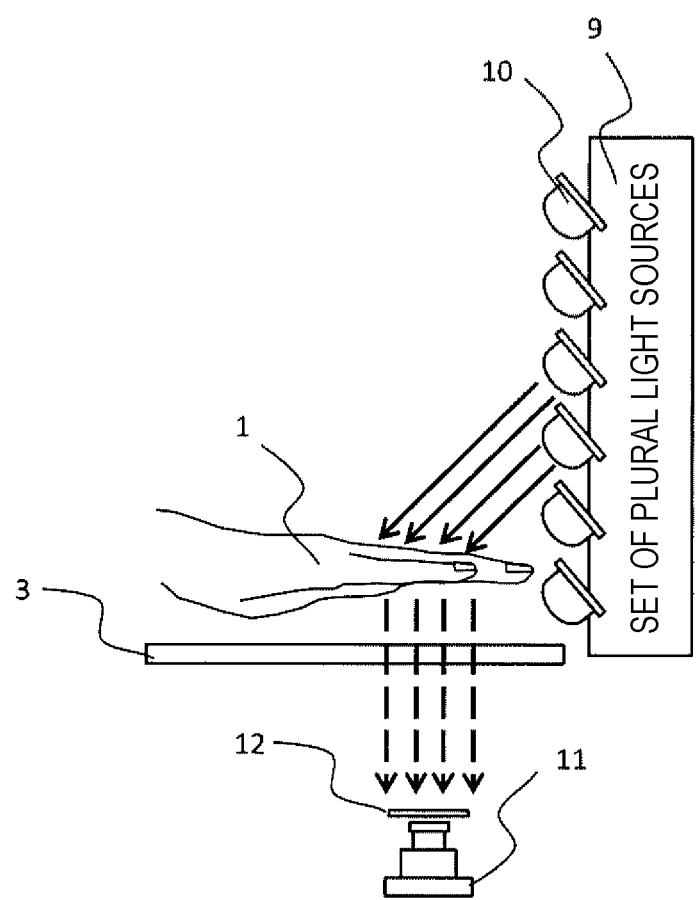
FIG. 3 is an example of a case where an image of a blood vessel in a finger is captured by irradiating the finger with irradiation light of light sources.

A control method of the light source array 9 for capturing a clear blood-vessel image of fingers will be described. As to an image capturing method of a blood-vessel image of fingers, the blood-vessel image can be captured by irradiating fingers on the back side of a hand with irradiation light (near infrared light) from the light source array 9 and receiving the light passing through the fingers by the image capturing portion 11 as illustrated in FIG. 3. Here, a reason why the light source array 9 needs to be controlled in capturing the blood-vessel image of the fingers by the authentication apparatus 2 will be described. When capturing a blood-vessel image, a large amount of light passes through the opening portion in the case where all the point light sources 10 constituting the light source array 9 are turned on and the hand is not shown. Moreover, if the hand is shown while all the point light sources 10 are still on, the brightness of the region of the hand will be saturated and the region will be blown out highlights in a blood-vessel image captured by light reflected by the fingers or other portions than the fingers. If the exposure time is shortened or the light amount of each of the point light sources 10 is reduced in order to suppress the blown out highlights, the amount of light passing through the fingers will decrease, and, further, due to the presence of irradiation light from the point light sources 10 that has not passed through the fingers in the opening portion, the captured blood-vessel image will be unclear. In addition, since not only a finger but also the whole hand including the palm and so forth can be shown at the opening portion 3 according to the present configuration of the apparatus, it is desirable that the opening portion 3 has a much wider shape than in an apparatus for causing only a finger to be shown, and thus there is a higher possibility that light unnecessary for image capturing gets into the opening portion 3. Therefore, there is a higher risk that image capturing of passing light of a small amount that has passed through a finger is hindered.

Accordingly, the amount of light passing through fingers needs to be increased by irradiating only the fingers with the irradiation light from the light source array 9 in order to capture a clear blood-vessel image.

Figure 4:
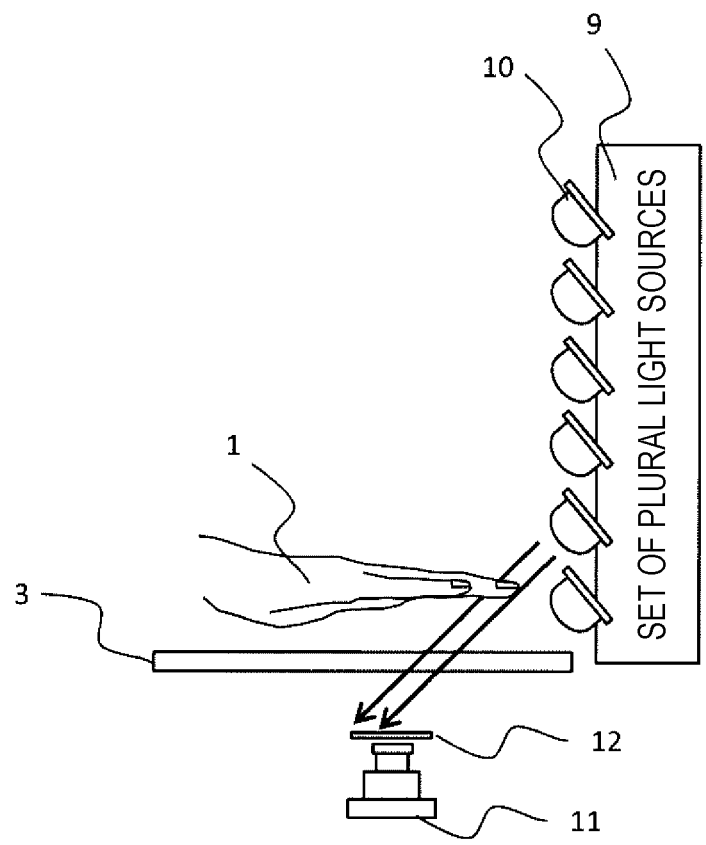
FIG. 4 is an example of a case where the irradiation light slips through between fingers when capturing the image of the blood vessel in the finger.
Figure 5:
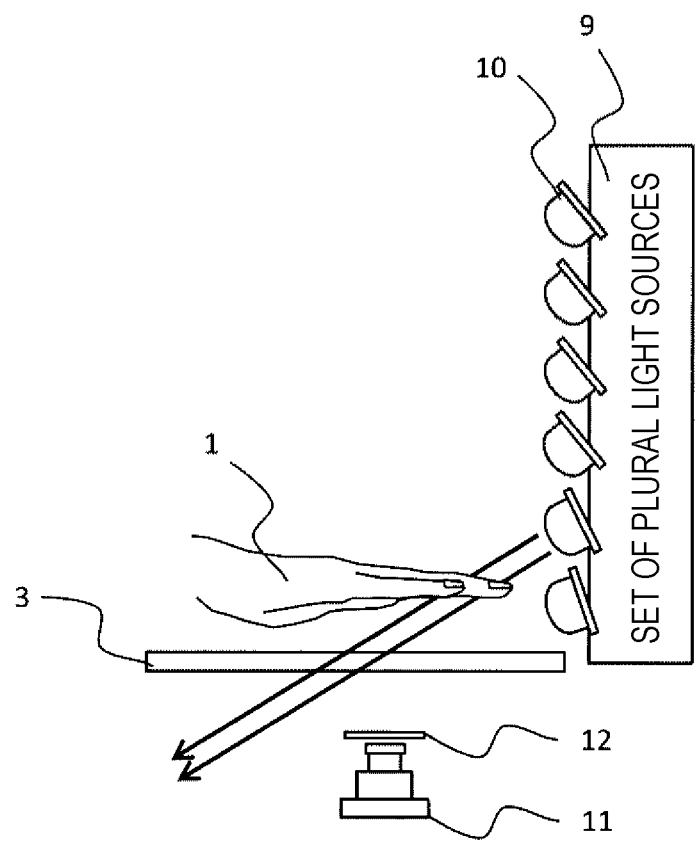
FIG. 5 is an example of arrangement of point light sources in which the irradiation light that has slipped through between the fingers is not directly received by an image capturing portion.

Although it is desirable that only the fingers are irradiated with light by controlling the light source array 9, irradiation light will slip through between fingers if it is attempted to irradiate plural fingers with light at the same time to capture an image of the plural fingers. For example, as illustrated in FIG. 4, a light source disposed at a position close to the opening portion has a high possibility of slipping through between fingers, and in the case where irradiation light of point light sources is directly received by the image capturing portion 11, blown out highlights (saturation of brightness) occur, and no clear blood-vessel image can be obtained. Considering this, in order to reduce the possibility of the image capturing portion 11 directly receiving the irradiation light even in the case where the irradiation light gets into the opening portion without irradiating a finger as illustrated in FIG. 5, it is desirable that each light source is disposed such that the acute angle formed by the optical axis of the light source and the opening plane of the opening portion is smaller for a light source closer to the opening portion, in other words, for a light source disposed at a lower position with respect to the surface on which the apparatus is placed. This configuration reduces the possibility of occurrence of brightness saturation, and enables capturing a clearer image of a blood vessel.

Figure 6:
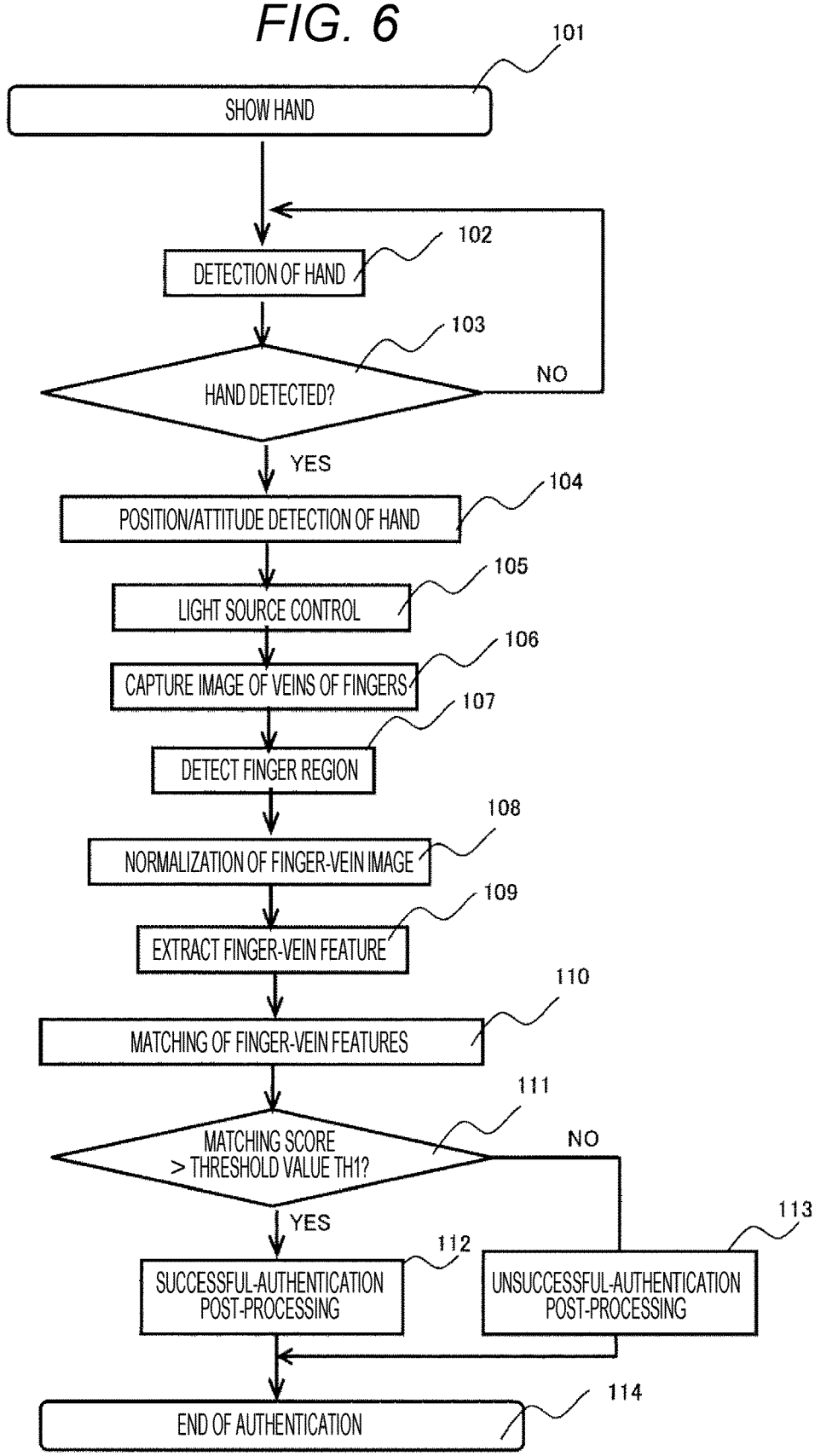
FIG. 6 is a flowchart of authentication processing that utilizes a blood-vessel image of the fingers captured by controlling the light sources.

FIG. 6 illustrates a flowchart of authentication processing that utilizes a blood-vessel image of fingers captured by controlling the amount of irradiation light from the light source array 9. First, in 101, an authenticating person shows a hand above the opening portion 3, and the hand is detected in 102. The hand is detected from distance data obtained by the distance sensor 4, and, in 103, it is determined whether the hand has been detected. In the case where the hand has not been detected, detection of hand of 102 is performed again. In the case where the hand has been detected, processing of detecting the position and attitude of the hand of 104 is performed. In other words, position information and attitude information based on the three-dimensional shape of the hand are detected and obtained. In accordance with the position of the hand and the attitude of the hand detected in 104, the light source array 9 is controlled in 105, and just point light sources for capturing a blood-vessel image of the fingers are selected and turned on as an irradiation light source. After turning the irradiation light source on, the image capturing portion 11 captures the blood-vessel image of the fingers in 106. Next, plural finger regions are detected in the blood-vessel image of the fingers in 107, and normalization processing, such as rotation correction of the fingers and correction of distortion resulting from variation of the attitude of the fingers in each finger region, is performed in 108. After normalization of the blood-vessel image of the fingers, a blood-vessel feature is extracted from each blood-vessel image of the fingers in 109. Matching score is calculated by matching the blood-vessel feature extracted in 110 with a blood-vessel feature already registered in the storage device 14. In the case where the matching score is larger than a predetermined threshold value TH1 in 111, 112 successful-authentication post-processing is performed, and, in the case where the matching score is equal to or smaller than TH1, unsuccessful-authentication post-processing is performed in 113. Then, the authentication flow is finished.

Figure 7:
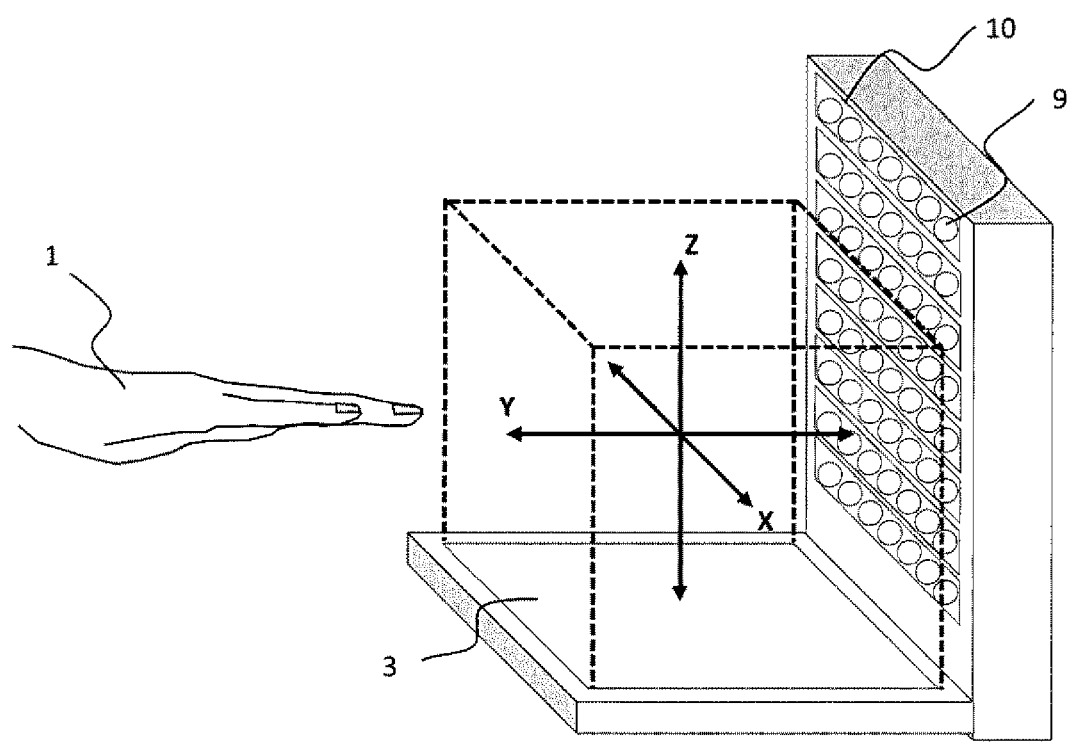
FIG. 7 is an explanatory diagram of a space in which a user shows a hand in authentication.

A control method of the light source array 9 to capture a clear blood-vessel image of a finger according to a position variation and an attitude variation of a hand or finger will be described. First, the position variation and attitude variation of the hand or finger in the authentication apparatus of FIG. 1 will be described. A space in which the hand is shown in the apparatus of FIG. 1 is desirably in a space (apparatus width direction: X, apparatus depth direction: Y, and apparatus height direction: Z) enclosed by broken lines in FIG. 7, and it is assumed that the palm side of the hand faces down and plural fingers are shown at the same time. Accordingly, as to the position variation of the hand, the position of the hand moves in each direction of three axes of an apparatus width direction, an apparatus depth direction, and an apparatus height direction. As to the attitude variation of the hand, there are an attitude variation according to rotation about each of three axes of an X axis, a Y axis, and a Z axis and an attitude variation of a finger in a three-dimensional space such as bending or warping of a finger. Lighting control of the light source array 9 in the case where the hand moves in each direction of the X axis, Y axis, and Z axis described above is performed by turning only point light sources 10 that radiate light that passes through a finger in accordance with a showing position of the hand or the finger.

In the case of changing the point light sources 10 to be turned on, that is, the irradiation light source, in accordance with a detected showing position of the plural fingers, sometimes the point light sources 10 to be turned on keep on changing and clear blood-vessel images cannot be stably obtained due to fluctuations in detected positions of the fingers even when the fingers are shown at the same position. To address this, the point light sources 10 to be turned on to capture clear blood-vessel images of plural fingers can be determined by controlling the light source array 9 on the basis of the average of detected positions of the plural fingers or the overall position of the hand which can be stably detected.

Figure 8:
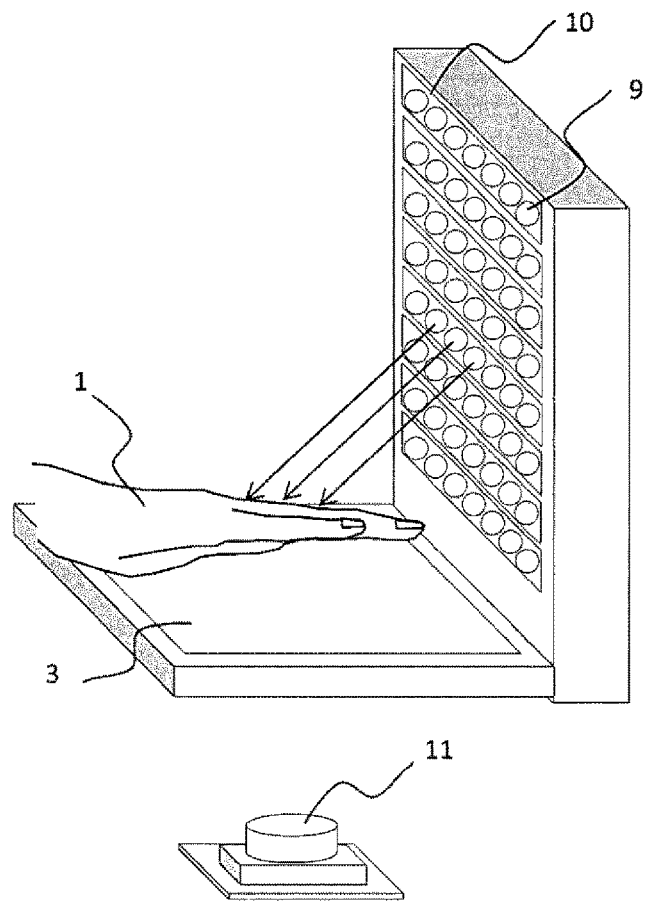
FIG. 8 is an example of a case where a hand is shown such that a tip of a finger is pointed to the front of a light source array and an image of a blood vessel in the fingers is captured.
Figure 9:
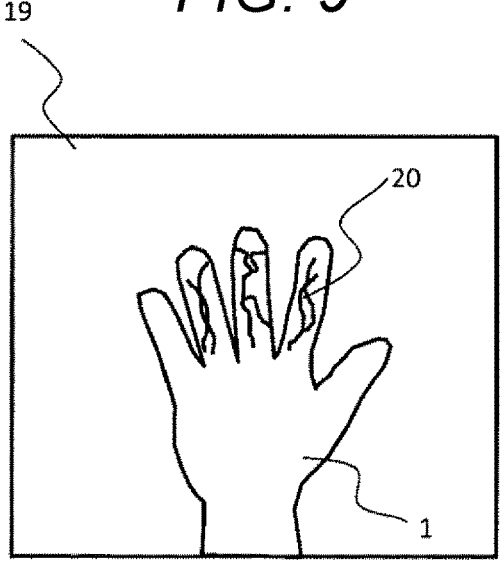
FIG. 9 is an example of the blood-vessel image of the fingers captured in FIG. 8.
Figure 10:
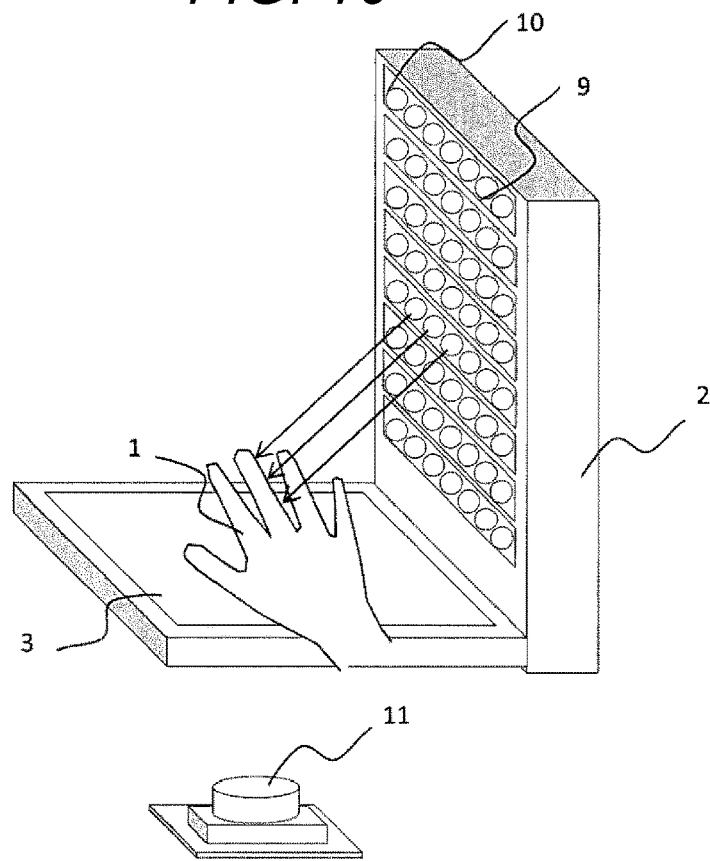
FIG. 10 is an example of a case where the hand is rotated by about 90 degrees on an image capturing plane from the showing attitude of the hand shown in FIG. 8.
Figure 11:
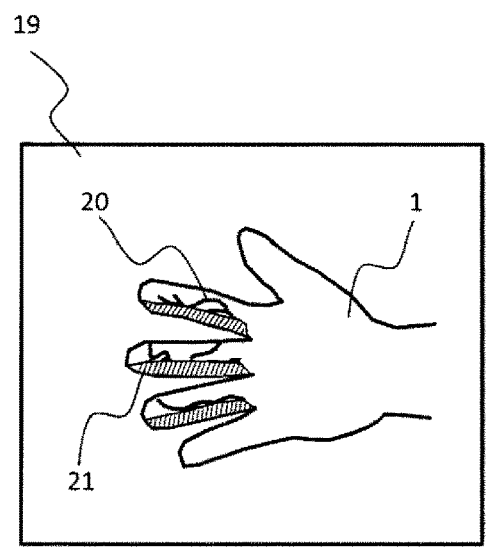
FIG. 11 is an example of the blood-vessel image of the fingers captured in FIG. 10 including a brightness saturation region.
Figure 14:
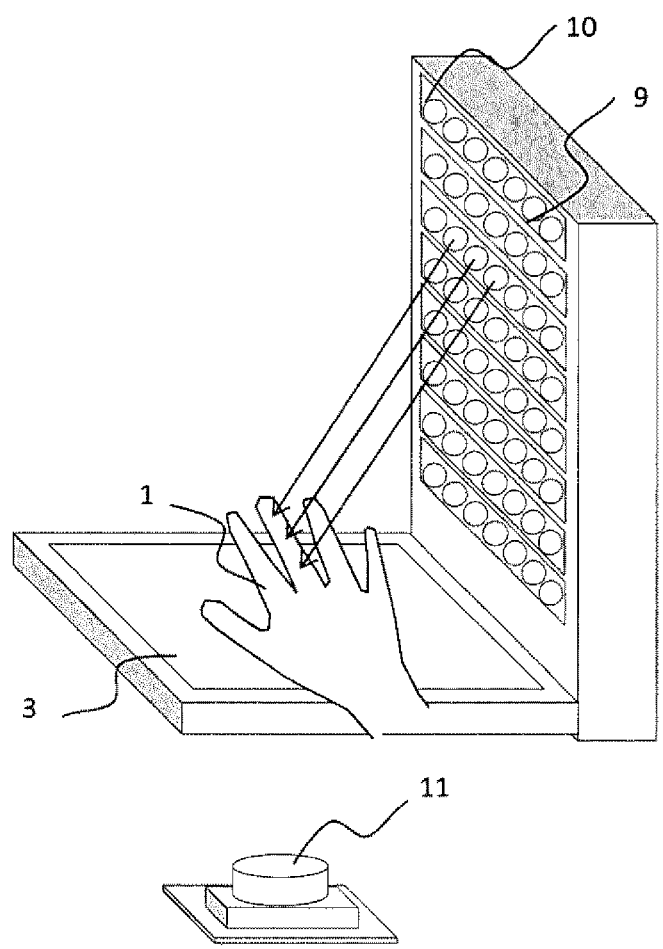
FIG. 14 is an example of a case of reducing the brightness saturation region of the blood-vessel image of the fingers by raising the position of an irradiation light source.

A lighting control method of the light source array 9 according to the attitude variation of the hand resulting from rotation will be described. In an example of FIG. 8, the hand is shown so as to point the fingertips to the front of the light source array 9. Here, it is assumed that finger blood vessels 20 of the hand 1 are captured in a blood-vessel image 19 captured by the image capturing portion 11 as illustrated in FIG. 9. The hand can be shown in various attitudes with respect to the authentication apparatus 2. Therefore, in the case where the hand is rotated and shown on an image capturing plane of the image capturing portion 11 as illustrated in FIG. 10, an irradiation direction of the point light sources 10 of the light source array 9 and the positions of the fingers change. In the example of FIG. 10, the hand is rotated by about 90 degrees on the image capturing plane from the showing attitude of the hand of FIG. 8, and the fingers are irradiated with irradiation light from point light sources 9 at the same height and the same irradiation angle. In the showing attitude of the hand of FIG. 8, a clear image of blood vessels of the fingers can be captured (FIG. 9). By contrast, since the image capturing portion 11 receives the irradiation light from the point light sources 10 reflected on the side surfaces of the fingers in the attitude of the hand of FIG. 10, brightness saturation regions 21 occur on one half-side of the fingers of the hand 1 in the blood-vessel image 19 captured by the image capturing portion 11 as illustrated in FIG. 11. To address this, in the case where the irradiation direction of the point light sources 10 and the direction of the fingertips of the shown hand are perpendicular to each other on the image capturing plane as illustrated in FIG. 14, the brightness saturation of the one half-side of the fingers can be suppressed by raising the point light sources 10 for irradiation to reduce the light with which the side surfaces of the fingers are irradiated.

Figure 12:
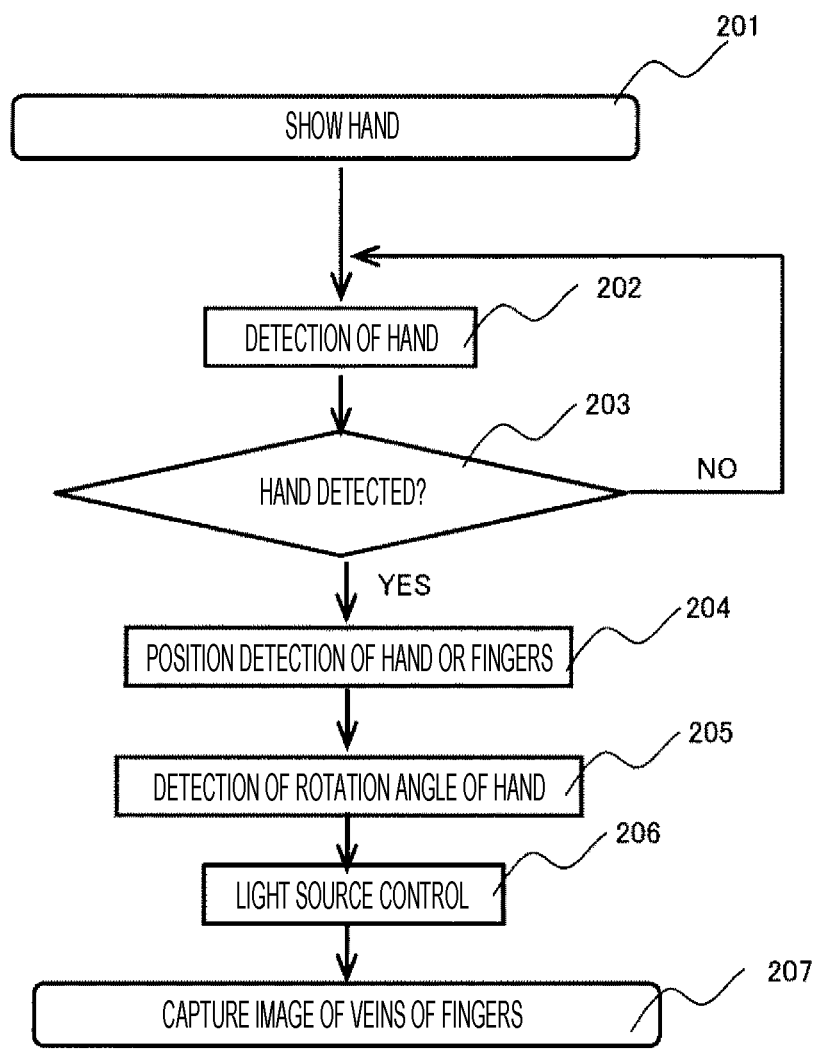
FIG. 12 is an example of a flowchart of capturing an image of blood vessels in the fingers by controlling light sources in accordance with the rotation of a hand.

FIG. 12 illustrates an example of a flowchart of capturing a blood-vessel image of fingers by controlling the lighting of the light source array 9 in accordance with the rotation of the shown hand. In 201, an authenticating person shows a hand to the authentication apparatus 2, and, in 202, the shown hand is detected. In 203, it is determined whether the hand has been detected. In the case where the hand has not been detected, the process returns to the detection of the hand of 202. In the case where the hand has been detected, processing of detecting the position of the hand and fingers is performed in 204. Next, in 205, the rotation angle of the hand is calculated from the detected hand and fingers. In 206, lighting control of the light source array 9 is performed by using the position of the fingers detected in 204 and the rotation angle of the hand calculated in 205, and only point light sources 10 that are not likely to irradiate the side surfaces of the fingers and can radiate light for capturing a clear image of blood vessels of the fingers are turned on. After turning the point light sources 10 on, the image capturing portion 11 captures a blood-vessel image of the fingers in 207. There are various methods for the method of calculating the rotation angle of the hand in 205. For example, it is desirable to calculate the center of the palm and the average (average direction of fingertips) of directions in which the fingertips point, and set the angle formed by the center of the palm and the average direction of fingertips as the rotation angle of the hand. For example, if the rotation angle is calculated from the fingers themselves, there is a high possibility that an error occurs in the rotation angle because fingers have many joints and thus there is a large variation in the attitudes thereof. By contrast, if the rotation angle of the hand is derived from the positional relationship between the palm and the directions in which the fingers are present, which has a relatively small attitude variation of variation, it becomes possible to derive the rotation angle at a higher precision than in the case where calculation is performed by setting the fingers themselves as a target. Details of the light source array control method of 206 will be described. First, the state where the average direction of fingertips points to the front of the light source array as illustrated in FIG. 8 is set as a standard position (angle of 0 degrees) of the rotation angle, and the rotation angle of the state where the average direction of fingertips points perpendicular to the standard position as illustrated in FIG. 10 is set as 90 degrees. As the rotation angle of the shown hand is increased from 0 degrees to 90 degrees, the light with which the side surfaces of the fingers are irradiated becomes stronger. Accordingly, the point light sources 10 for irradiation are provisionally determined in accordance with the positions of the shown fingers, and, further, point light sources 10 at higher positions than the provisionally determined point light sources 10 are turned on in accordance with the rotation angle of the hand such that the side surfaces of the fingers are not irradiated with light. As to the height of the point light sources 10 to be turned on corresponding to the rotation angle of the hand, point light sources 10 of which height are to be turned on can be determined in advance to be proportional to the rotation angle.

Figure 13:
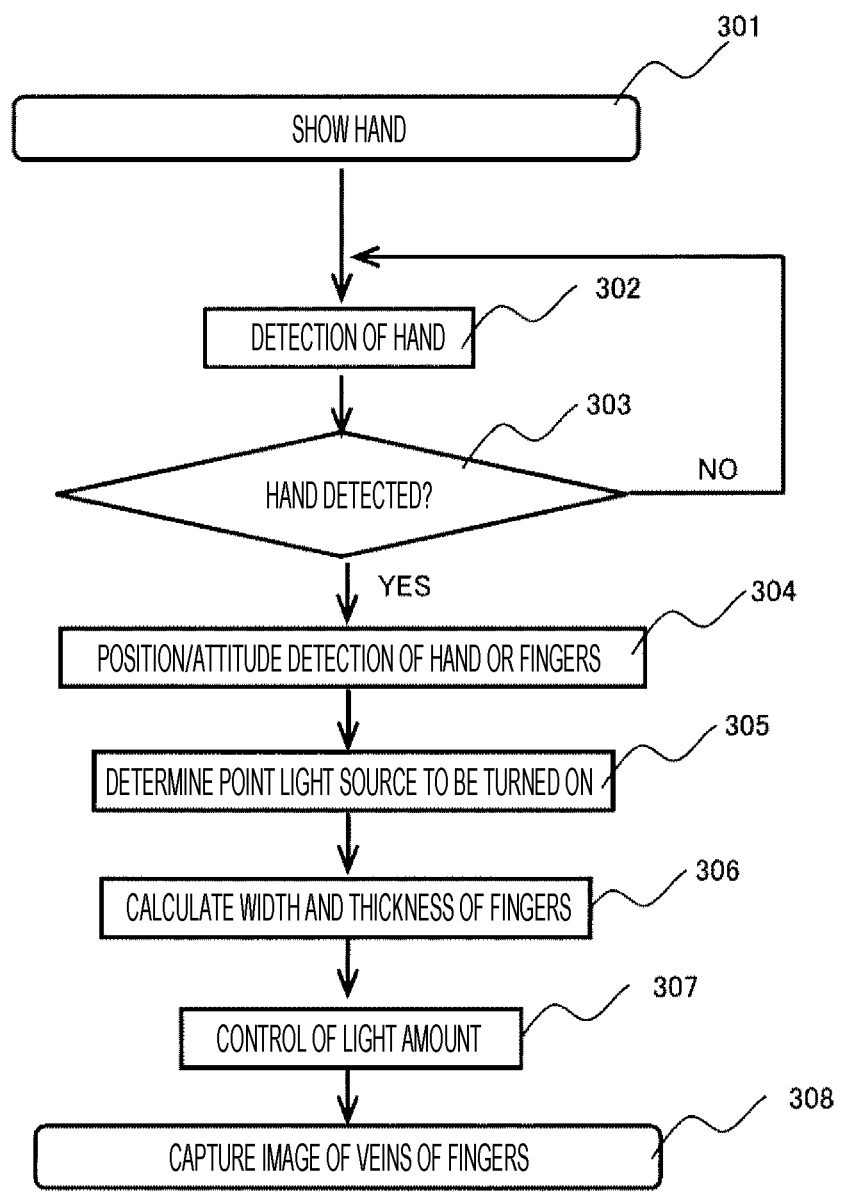
FIG. 13 is an example of a flowchart of capturing an image of blood vessels in the fingers by controlling a light amount of the light sources in accordance with the size of a hand.

As to light amount control of the point light sources 10 to be turned on, irradiation can be performed at a constant light amount regardless of the size of the hand. However, generally, the bigger the hand is, the larger the width and the thickness of the fingers become and light becomes less likely to be transmitted. Accordingly, a clear blood-vessel image can be captured regardless of the size of the hand by controlling the amount of light to be radiated in accordance the width and the thickness of the fingers. FIG. 13 illustrates an exemplary flowchart of a process of controlling the light source array 9 on the basis of information of the position and attitude of the hand, controlling the light amount of the point light sources 10 in accordance with the size of the hand, and capturing an image of blood vessels in fingers. In 301, an authenticating person shows a hand to the authentication apparatus 2, and, in 302, the shown hand is detected. In 303, it is determined whether the hand has been detected. In the case where the hand has not been detected, the process returns to the detection of the hand of 302. In the case where the hand has been detected, processing of detecting the position and attitude of the hand and fingers of 304 is performed. In 305, point light sources 10 to be turned on of the light source array 9 is determined on the basis of the detection result of the position and attitude of 304. In 306, the width and thickness of the fingers are calculated from the detected attitude of the hand and fingers detected in 304 and the distance data obtained by the distance sensor 4. In 307, light amount control of the point light sources 10 to be turned on is performed on the basis of the width and thickness of fingers calculated in 306, and a blood-vessel image of the fingers is captured in 308. Since it is difficult to measure the precise thickness of the fingers by only using the distance sensor 4 in the calculation of the width and thickness of the fingers in 306, the light amount may be controlled by using only the width of the fingers in 307. In addition, as a substitute means for thickness measurement of the fingers, the thickness of the fingers can be estimated from the shape and size of the hand and fingers that can be measured by using the distance sensor 4. For example, the thickness of the fingers can be estimated from the length and the width of the fingers. In addition, the thickness of the fingers can be estimated from the overall size of the hand or the size of a palm region. As to a light amount control method that utilizes the estimated thickness of the fingers, a thickness of fingers serving as a standard and an irradiation light amount for the thickness of fingers are determined in advance, and an irradiation light amount can be determined in accordance with the ratio between the thickness of the fingers of the shown hand and the thickness of fingers serving as the standard. In addition, in the case where the shown hand is at the same position as at the time of capturing a blood-vessel image of a previous frame (is still), feedback control of light amount can be performed by performing excess/deficiency determination of light amount from an average brightness of a finger region of a blood-vessel image captured by the image capturing portion 11 and by utilizing the result of the determination.

As to light amount control according to the distance between the fingers and the point light sources 10 to be turned on, in the case where irradiation light scatters greatly in accordance with the distance such as where the point light sources 10 are LEDs, the amount of light radiated onto the fingers becomes smaller and thus the amount of light passing through the fingers becomes smaller as the distance between the point light sources 10 and the fingers becomes larger when the point light sources 10 are lighted at the same light amount value. To address this, the irradiation light amount of the point light sources 10 is controlled in accordance with the distance between the fingers and the point light sources 10 such that a constant amount of light is radiated onto the fingers.

Figure 15:
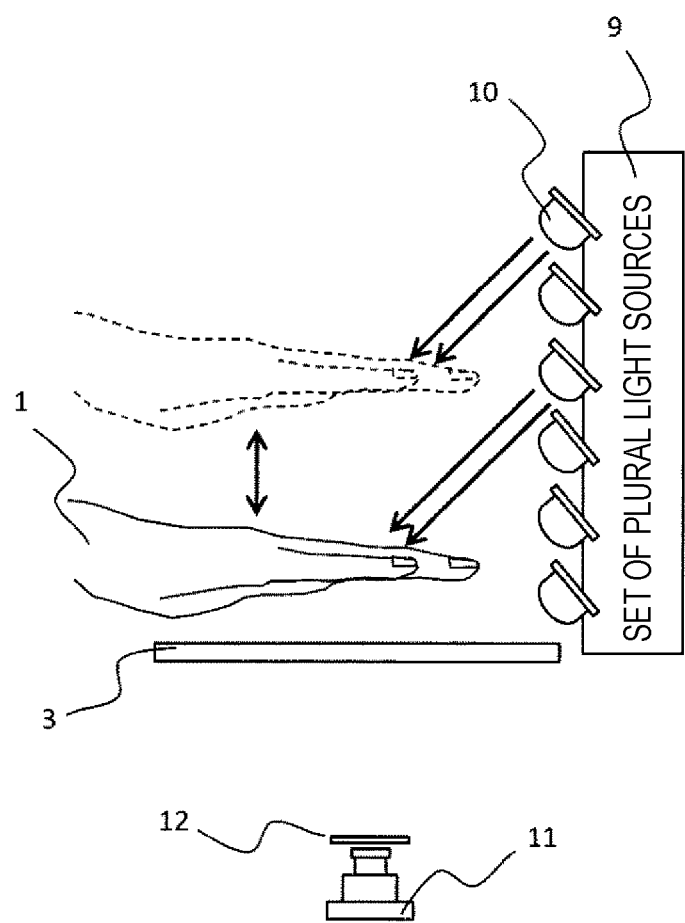
FIG. 15 is an example of a case of capturing the image of the blood vessels in the fingers in accordance with movement of the hand in a height direction of the authentication apparatus.
Figure 16:
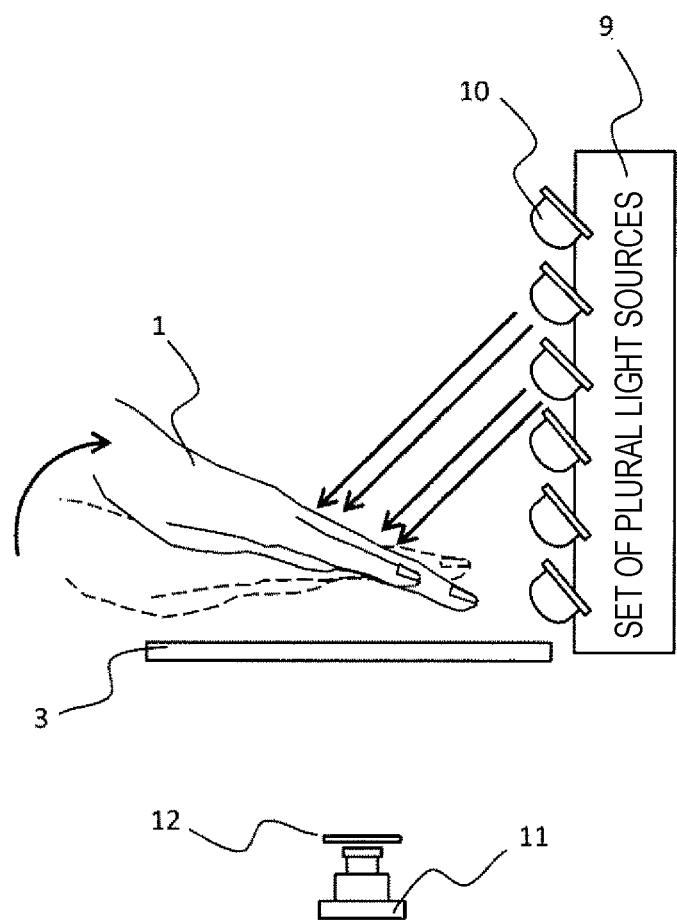
FIG. 16 is an example of a case where the hand is inclined with respect to the image capturing plane with the light sources arranged as in FIG. 15.

A light amount control method of the light source array 9 for capturing a clear blood-vessel image in accordance with an attitude variation of inclining the hand or the fingers with respect to a finger-blood-vessel image capturing plane (X-Y plane) will be described. A point light source arrangement of the light source array 9 of FIG. 15 is an example in which, in the case where the hand is moved in the apparatus height direction (Z axis direction) with an attitude of the hand being horizontal with respect to the image capturing plane of the image capturing portion 11, the irradiation angle of each point light source is adjusted such that a clear image of blood vessels of the fingers can be captured even when the height at which the hand is shown is changed. This is because the amount of light radiated from the point light sources 10 and passing through the fingers does not change. However, when the horizontal attitude of the hand of FIG. 15 is changed to an attitude in which the palm is inclined as illustrated in FIG. 16, the amount of irradiation light of the point light sources passing through the fingers changes (in this example, the amount of passing light increases), and thus the brightness is saturated and a dark and unclear blood-vessel image is captured. To address this, light amount control is performed in accordance with the inclination attitude of the hand such that the amount of passing light of the point light sources 10 passing through the fingers becomes constant, and a clear blood-vessel image of the fingers is captured.

When the point light sources 10 are always lighted at a constant light amount, even if a clear blood-vessel image can be captured with the attitude of the hand of FIG. 14, the amount of light passing through the fingers increases when the attitude changes to the attitude of the hand of FIG. 15 and the brightness is saturated in a blood-vessel image. Therefore, it becomes possible to capture a clear image of blood vessels of the fingers by reducing the irradiation light amount of the point light sources 10 to be turned on.

Second Exemplary Embodiment

In the first exemplary embodiment, an arrangement method of light sources and a control method of light amount for suppressing the occurrence of a brightness saturation region in a captured image have been described. In the present exemplary embodiment, a control method of light sources for further reducing the possibility of occurrence of the brightness saturation region will be described.

In the case where a position or attitude variation of the hand or the fingers has occurred, it is desirable that the selection of the irradiation light source is performed such that a light source that is less likely to cause the saturation region is selected from among the light sources for irradiating the fingers with light. In the present exemplary embodiment, a method paying attention to a portion of fingers to be irradiated with the irradiation light from the point light sources 10 will be described as a selection method that is less likely to cause the brightness saturation region.

Figure 17:
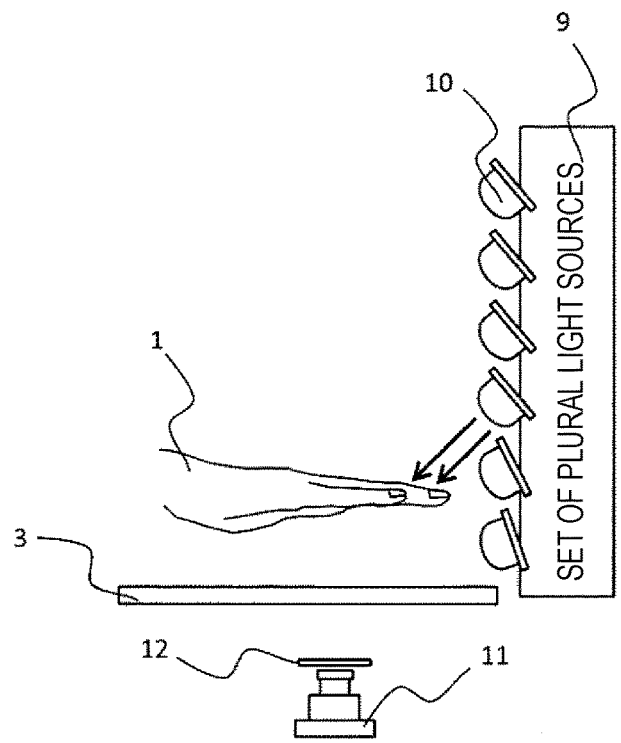
FIG. 17 is an example of a case where a portion near first joints of the fingers is irradiated when capturing the blood-vessel image of the fingers.
Figure 18:
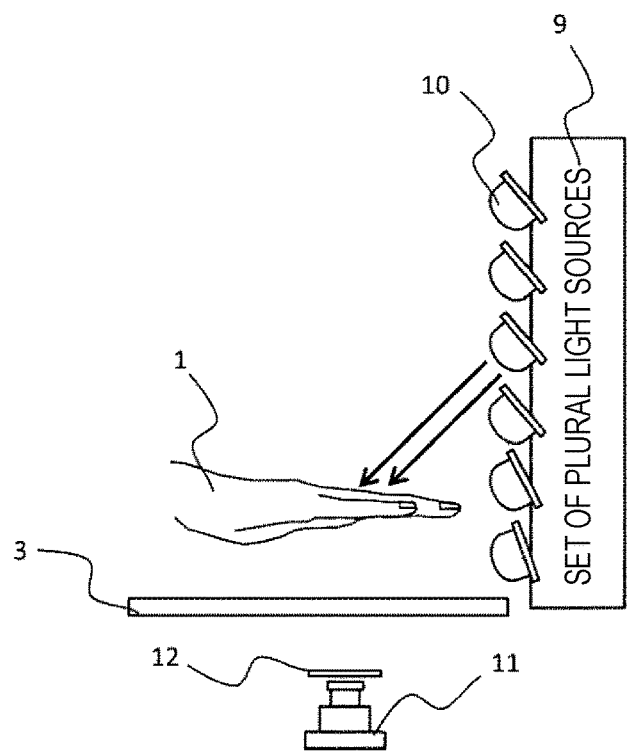
FIG. 18 is an example of a case where a portion near second joints of the fingers is irradiated when capturing the blood-vessel image of the fingers.

For example, in the case where the portion of the fingers irradiated with light is contrasted between the root side and the fingertip side, on the fingertip side of the fingers, the space between fingers is wider than on the root side of the fingers as illustrated in FIG. 17, and thus the amount of light with which the fingertip side is to be irradiated but slips through between fingers becomes larger and the image quality of the blood-vessel image is lowered. In addition, in the case where the vicinity of the fingertips of the fingers is irradiated intentionally, the image capturing portion not only receives a large amount of irradiation light slipping through between fingers, but also is likely to receive light reflected on the fingertips or side surfaces of the fingers in addition to the light passing through the fingers, and saturation of brightness occurs in the fingertips and a side surface region of the fingers in an image of blood vessels in the fingers captured by the image capturing portion 11. By contrast, by irradiating the vicinity of the second joints of the fingers that are on the root side of the fingers as illustrated in FIG. 18, the image quality deterioration of the blood-vessel image can be suppressed because the irradiation light slipping through between the fingers is reduced and the light is radiated onto joint positions at which the light is likely to pass through. Further, even if the portion of the fingers irradiated with light from the point light sources 10 is a little displaced toward the root of the fingers, the image capturing portion 11 below the shown hand does not receive excessive light and the image quality deterioration of the blood-vessel image can be suppressed because the irradiation light is reflected or absorbed by the back of the hand.

Third Exemplary Embodiment

In the first exemplary embodiment, light sources arranged in a lattice pattern in the light source array 9 has been described to expand the freedom of the showing attitude of the hand. Another exemplary embodiment of an arrangement method of the light sources for improving the precision of the captured image while improving the usability concerning the showing attitude will be described. To be noted, the present exemplary embodiment can be implemented individually from the light amount control of the first and second exemplary embodiments as long as plural light sources are arranged in a lattice pattern.

Figure 19:
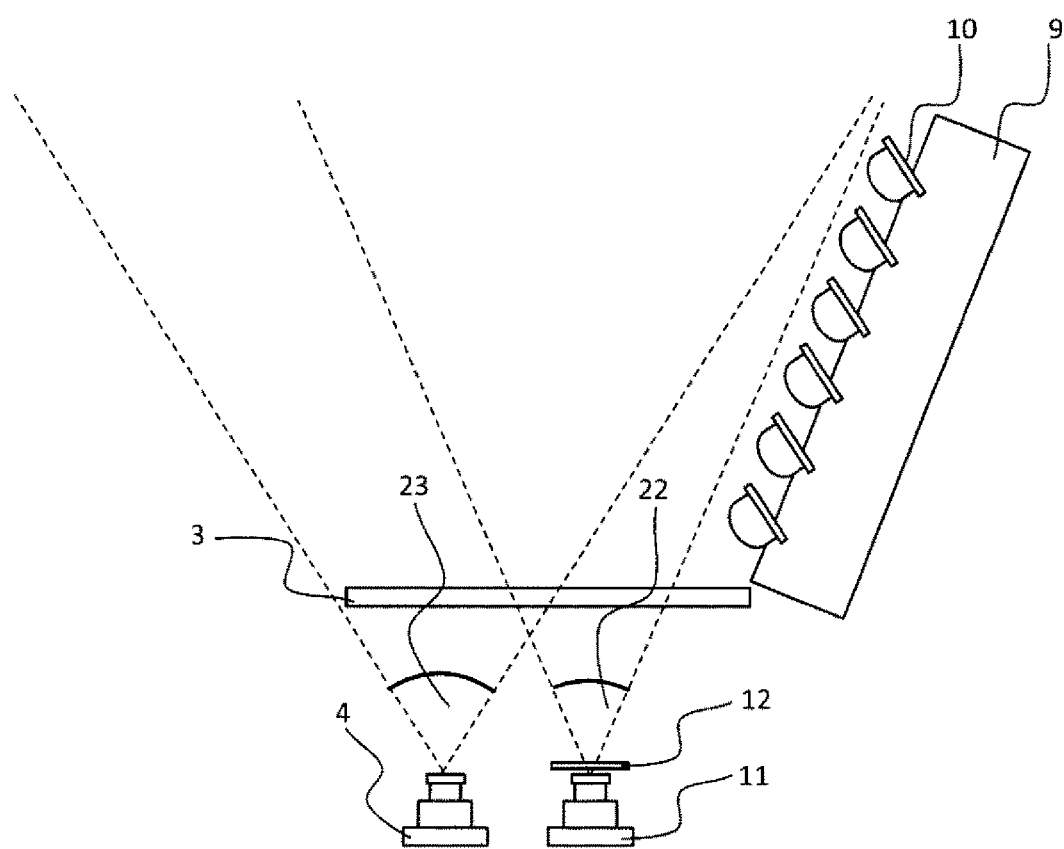
FIG. 19 is an example of a case where the light source array is disposed in a position out of an angle of view of the image capturing portion and a distance sensor.

As to the arrangement positions of the point light sources 10 constituting the light source array 9 according to the present exemplary embodiment, the point light sources 10 can be arranged so as not to be in an angle of view 22 of the image capturing portion 11 (in other words, in an image capturing range of the image capturing portion 11) or an angle of view 23 of the distance sensor 4 (in other words, a detection range of the distance sensor 4) without being arranged in a substantially vertical direction with respect to the opening portion 3 as illustrated in FIG. 3 of the first exemplary embodiment such that the light source array 9 is inclined so as to be out of the angles of view as illustrated in FIG. 19. When the light source array 9 gets in the angle of view 22 of the image capturing portion 11, a light source part becomes bright when the light sources are turned on. This may cause brightness saturation and lower the overall clearness of the blood-vessel image. This is a phenomenon unique to the light sources of the authentication apparatus 2 in which the light sources becomes likely to get in the range of angles of view of the image capturing portion 11 and the distance sensor 4 as a result of the plural light sources being arranged in a lattice pattern in a vertical direction with respect to the surface on which the housing is placed. Accordingly, the light source array 9 getting captured in the image can be prevented and a clear blood-vessel image can be captured by disposing the light source array 9 so as to be inclined as illustrated in FIG. 19. In addition, when the light source array gets in the angle of view 23 of the distance sensor 4, the precision of the position detection and attitude detection of the hand or the fingers may be lowered in the distance measurement because of inclusion of a noise. Accordingly, by disposing the light source array 9 so as to be inclined as illustrated in FIG. 19, the point light sources 10 can be prevented from getting in the image, the precision deterioration of the position detection and attitude detection of the hand or the fingers can be prevented, and the occurrence of brightness saturation in the captured image can be suppressed.

Fourth Exemplary Embodiment

A method of detecting the position and attitude of the hand by simultaneously performing distance measurement using near infrared light and blood-vessel image capturing of fingers using near infrared light in the configuration of the authentication apparatus 2 of the first exemplary embodiment will be described. In the case where the distance sensor 4 performs distance measurement by using reflection of near infrared light by using, for example, a time of flight (ToF) method, the near infrared light radiated upward from the distance sensor 4 passes through the opening portion 3, is reflected on the surface of the hand 1, passes through the opening portion 3 again, and is received by the distance sensor 4 as a result of a transparent material such as acrylic resin or glass being used for the opening portion 3. Since also near infrared light radiated from the light source array 9 is used for capturing the blood-vessel image of the fingers, the near infrared light for distance detection and the near infrared light for blood-vessel image capturing interfere with each other, and distance detection and blood-vessel image capturing cannot be performed simultaneously. To address this, different wavelengths are selected for the light for distance detection and the light for blood-vessel image capturing to suppress the interference between the wavelengths. Further, by using the optical filter 12 to cut off light of a wavelength region for distance detection to let only light of a wavelength region for blood-vessel image capturing pass through before the image capturing portion 11 that performs blood-vessel image capturing receives light, distance detection and blood-vessel image capturing can be performed simultaneously in the distance detection and the blood-vessel image capturing even though near infrared light is used for each of these. To give a specific wavelength range as a mere example, it is desirable for the wavelength range for simultaneously performing distance measurement and blood-vessel image capturing that the distance sensor 4 utilizes light of a wavelength region in a range from 830 nm to 870 nm, the light source array 9 utilizes a wavelength region of a range from 870 nm to 950 nm for the image capturing portion 11 to capture an image of blood vessels, and the optical filter 12 shields light of wavelengths shorter than an intermediate wavelength region between the wavelengths selected for the distance sensor 4 and the light source array 9 before the image capturing portion 11 receives the light. To set the wavelength regions of the distance sensor 4 and the light source array 9 further away from each other, the distance sensor 4 can utilize a wavelength region of a range from 840 nm to 860 nm, and the light source array 9 can utilize a wavelength region of a range from 890 nm to 910 nm. At this time, the optical filter 12 that shields light of wavelengths shorter than a predetermined wavelength in a range from 860 nm to 890 nm is used. Further, by limiting wavelengths to be selected, the distance sensor 4 utilizing near infrared light of a wavelength region of 850 nm or 870 nm, setting the wavelength of the light source array 9 to 910 nm, and shielding light of wavelengths shorter than 900 nm by the optical filter 12, highly precise distance measurement and image capturing of a clear blood-vessel image can be performed simultaneously.

Alternatively, the wavelength of the light source array 9 can be selected from the range of 850 nm to 870 nm, and the wavelength of the distance sensor 4 can be selected from wavelengths shorter than 850 nm or wavelengths longer than 870 nm. At this time, the optical filter 12 that only lets wavelength light of the light source array 9 pass through and shields wavelength light of the distance sensor 4 is used.

Figure 20:
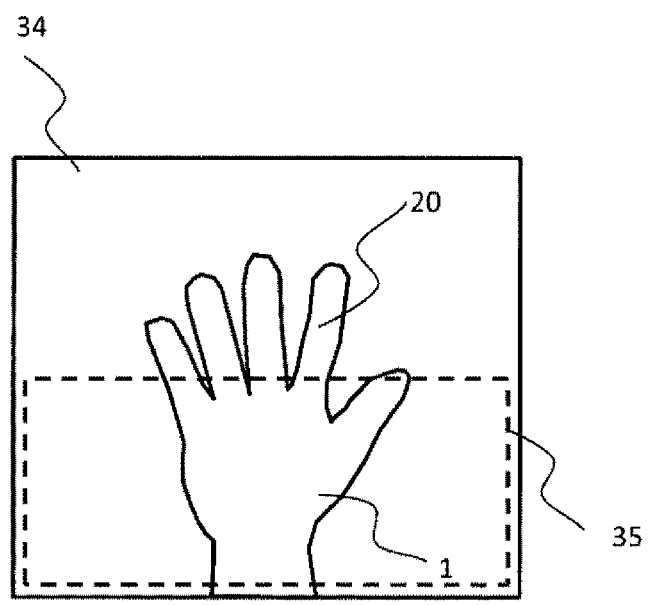
FIG. 20 is an example of a distance image of the hand captured by the distance sensor.
Figure 21:
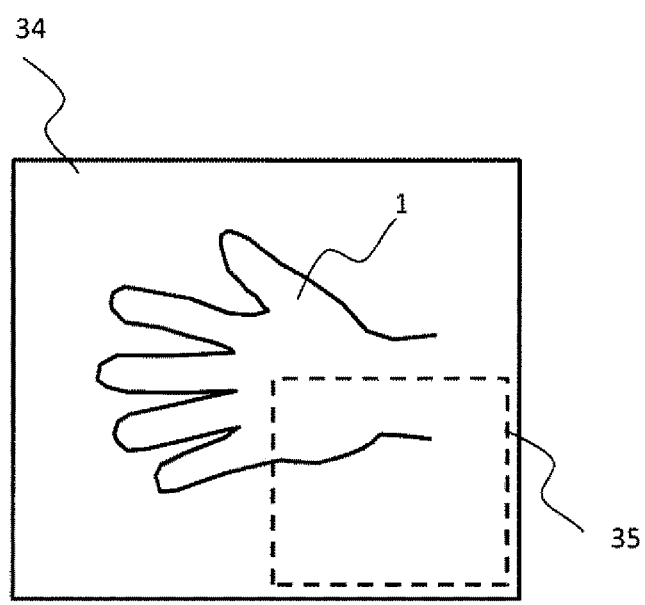
FIG. 21 is an example of a distance image of the hand captured by the distance sensor

As has been described above, the infrared light radiated upward for distance measurement of the distance sensor 4 of the ToF method passes through the opening portion 3 formed of a transparent material. However, at a position at which the optical axis of the irradiation light crosses the plane of the opening portion 3 at right angles, it may not be possible to perform measurement of distance because the irradiation light is reflected and received by the distance sensor 4 without passing through. To prevent the fingers from being shown at this position (distance unmeasurable point) at which the distance cannot be measured, a position at which the hand is likely to be placed can be statistically derived from experiments, and the distance sensor 4 can be disposed such that the distance unmeasurable point is placed not in the vicinity of the fingers but in the vicinity of the palm or the wrist. Specifically, it is assumed that a distance image obtained by the distance sensor 4 in the case where a user stands right in front of the light source array 9 and shows the hand above the opening portion 3 as illustrated in FIG. 8 is illustrated in FIG. 20. In this distance image, the fingers are likely to be shown on the upper-half side of the image, that is, on the side closer to the light source array 9 due to the positional relationship in the whole hand. Meanwhile, the palm is shown in the lower half of the distance image. Thus, the distance sensor 4 can be disposed such that the distance unmeasurable point is placed in the lower half of the distance image, that is, on the side farther from the light source array 9 and closer to the user. In addition, as will be described later, assuming that the user shows the hand to the authentication apparatus 2 for authentication while walking, a case where the direction of the hand shown by the walking user coincides with the moving direction of the user as illustrated in FIG. 10 can be considered in addition to the case where the fingers are shown on the side closer to the light source array 9 as illustrated in FIG. 8. At this time, in the distance image, the fingers are captured in the left half of the image and the palm is captured in the right half of the image as illustrated in FIG. 21. Accordingly, a setting range of the distance unmeasurable point can be set to a lower right region of the distance image divided into four such that the distance unmeasurable point is placed not in the vicinity of the fingers but in the vicinity of the palm in both showing positions of the hand illustrated in FIG. 8 and FIG. 10. In addition, to give description in view of the positional relationships between the light source array, the opening portion, and the distance sensor, the distance sensor is disposed at a position at which the distance from the distance sensor to the center of the opening portion is longer than the distance from the light source array including plural light sources to the center of the opening portion. To mention the relationships with the shown hand, it is desirable that the light source array is disposed on the fingertip side and the distance sensor is disposed on the palm side.

In addition, as another method, marking for guiding the showing position of the hand on the opening portion 3 can be provided such that not the fingers but the palm is shown at the distance unmeasurable point. By using a material that shields visible light and transmits near infrared light for this marking, there will be no adverse effect on capturing of a blood-vessel image of the fingers. By disposing a material that absorbs the irradiation light at the position (point) at which the optical axis of the light radiated upward from the distance sensor 4 crosses the plane of the opening portion 3 at right angles, the distance sensor 4 can be prevented from receiving the light reflected on the opening portion 3, and the region in which distance measurement cannot be performed can be minimized.

If distance measurement and blood-vessel image capturing can be captured simultaneously, the distance sensor 4 and the image capturing portion 11 can be synchronized by deriving correspondence (coordinate conversion) between respective pixels of the distance image (distance data) of the distance sensor 4 and the blood-vessel image captured by the image capturing portion 11. Accordingly, by converting positions of a region of the hand and a region of each finger detected from the distance image of the distance sensor 4 into positions in the blood-vessel image via coordinate conversion, the region of the hand and the region of each finger can be easily determined in the blood-vessel image. In the case of attempting to detect the region of the hand or fingers by using only the blood-vessel image, the blood-vessel image captured by the image capturing portion 11 includes the background different from the shown hand, and the hand is also shown in various positions or attitudes. Therefore, it is difficult to precisely detect the region of the hand or fingers only via image processing. By contrast, in the distance image that can be obtained by the distance sensor 4, it is easy to detect the region of the hand or fingers because there is a clear distance difference between the background and the region of the hand. That is, being able to reflect a detection result of a region/position of the hand or fingers using the distance image on the blood-vessel image leads to improvement of detection precision of the region/position of the hand or fingers. Parameters for converting the distance image (three-dimensional data) of the distance sensor 4 into the two-dimensional blood-vessel image captured by the image capturing portion 11 can be derived in advance, and examples of the parameters include the distance between optical axes of the distance sensor 4 and the image capturing portion 11, a rotation angle between the optical axes, the focal length of the distance sensor 4, and the focal length of the image capturing portion 11. These parameters can be derived by using methods such as stereo calibration. In stereo calibration, an object common to plural image capturing portions is captured plural times, and the above-described parameters are calculated from relationships between corresponding positions of the object. In the case where the distance sensor 4 utilizes a time of flight (ToF) method, stereo calibration can be performed by using a near infrared image obtained by the distance sensor 4 and a near infrared image captured by the image capturing portion 11 because plural near infrared images are captured when measuring the distance. Alternatively, a coordinate conversion parameter may be derived by performing stereo calibration between the distance data of the distance sensor 4 and the image data of the image capturing portion 11.

In the case where the distance sensor 4 is a disposed stereo camera constituted by plural cameras, there is no need to radiate light upward from a lower portion of the opening portion in distance measurement. Accordingly, there is no restriction in the wavelength of the light source array 9 and the wavelength can be freely selected, and distance measurement and image capturing of blood vessels in the fingers can be performed simultaneously by using only the irradiation light from the light source array 9. Further, by setting one or more cameras in plural cameras constituting the stereo camera as the image capturing portion 11, it becomes possible to perform distance measurement and image capturing of blood vessels in the fingers by the same cameras, and there is no longer need to perform coordinate conversion between the distance sensor 4 and the image capturing portion 11 that have different optical axes.

Figure 22:
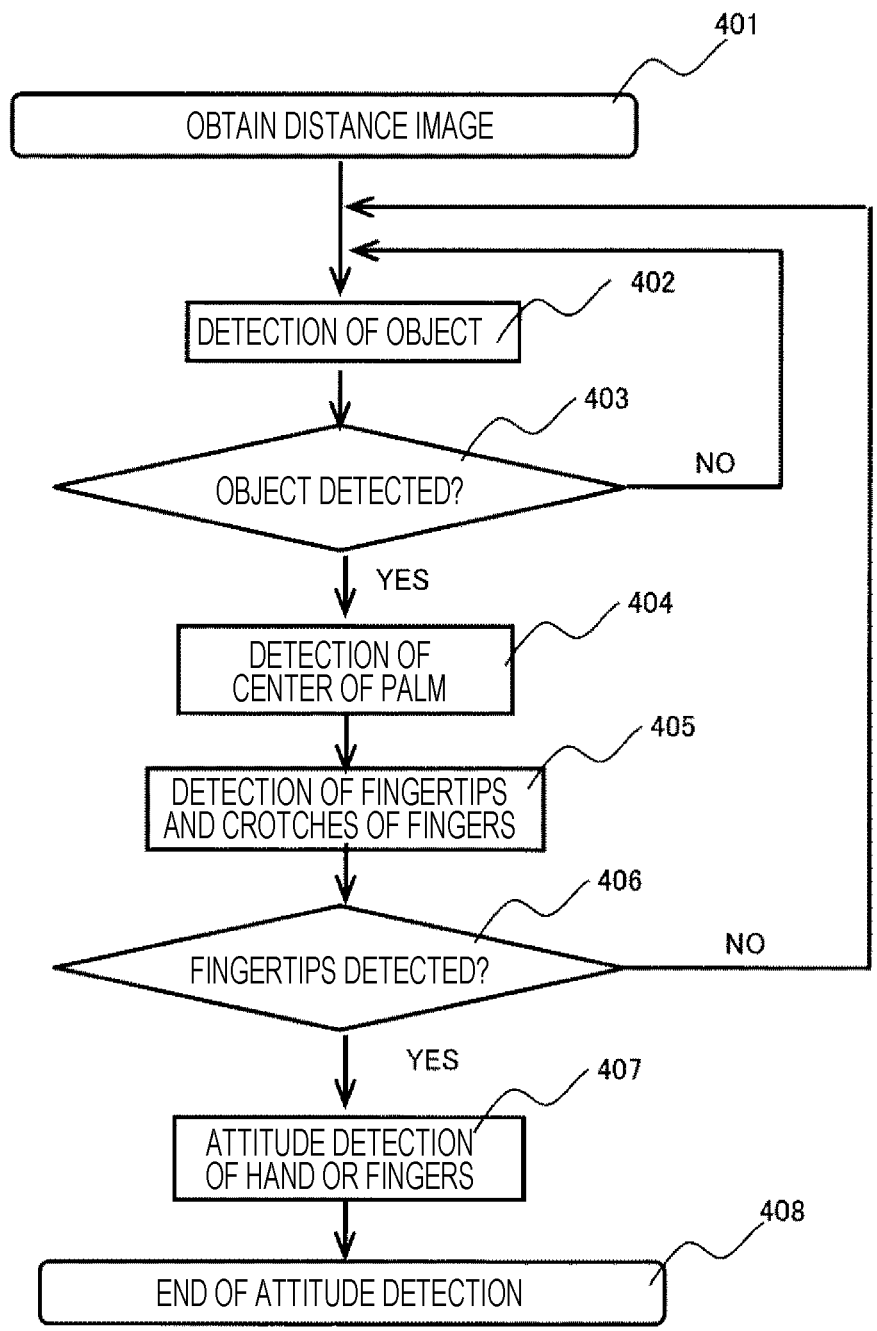
FIG. 22 is a flowchart of position/attitude detection processing of the hand using distance data.
Figure 23:
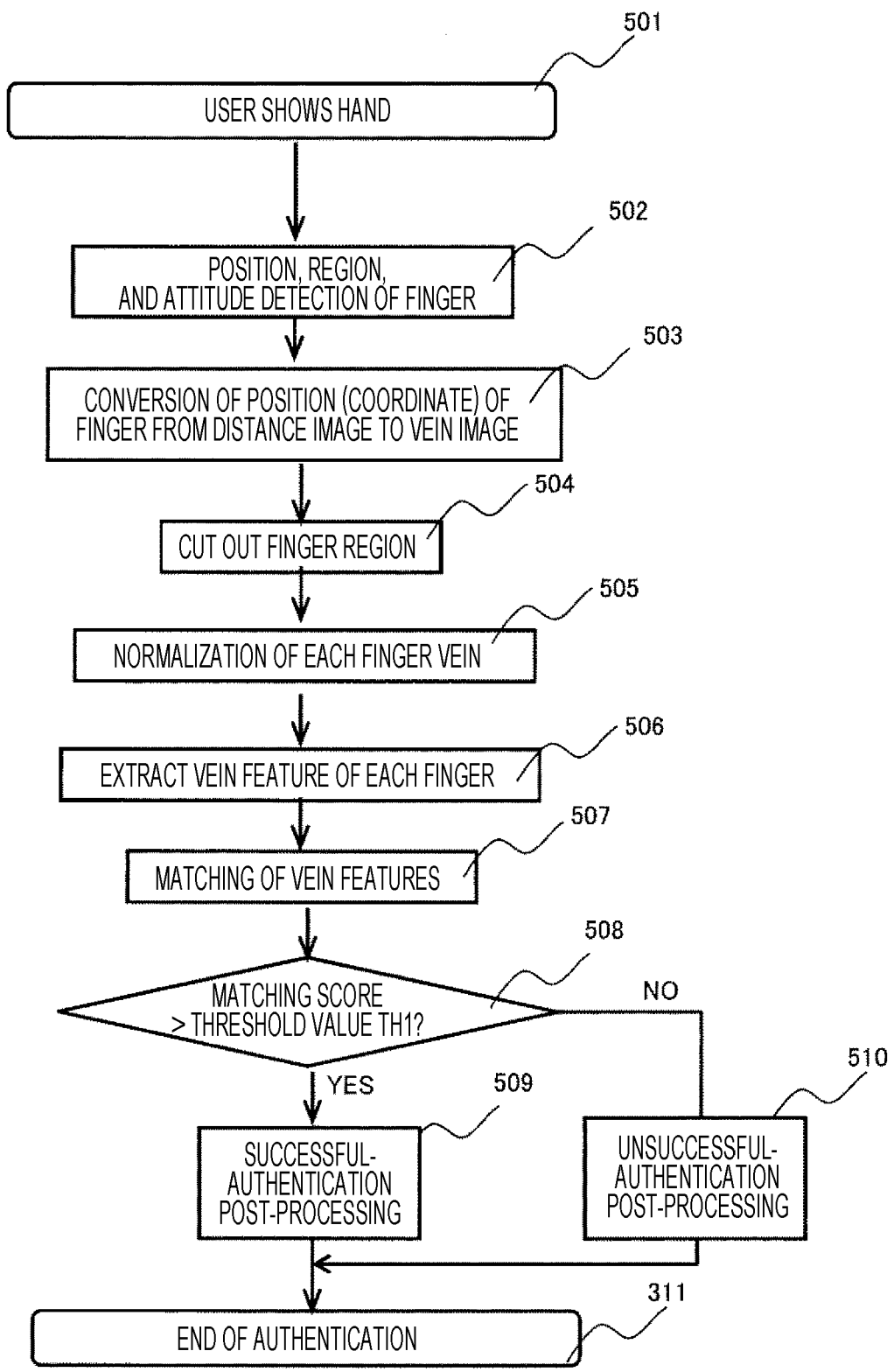
FIG. 23 is a flowchart of finger-blood-vessel authentication processing after detection of the attitude of the hand and the fingers.

An example of a means for detecting the position of the hand and the attitude of the hand from the distance data obtained by the distance sensor 4 in the authentication apparatus of FIG. 1 will be described in a flowchart of FIG. 22. First, the distance data obtained by the distance sensor 4 is converted into a distance image in which pixel values indicate distances in 401 before detection of the hand and detection of the attitude. In 402, an object present in a predetermined range of distance is detected in the distance image. For example, the object can be detected as a region of successive pixels that can be extracted by generating a histogram of all pixel values (distance values) of the distance image and keeping only distance values in the vicinity of a local maximum position of the histogram. In the case where the object has been detected in 403, detection of the center of the palm is performed in 404, and, in the case where the object has not been detected, the process returns to the object detection of 402. In the detection of the center of the palm of 404, an outline position of the object detected in 403 is smoothed by using, for example, morphology calculation, and an outline (closed curve) of the object is extracted. It is assumed that the derived outline is a region of the hand, and the center of a circle of the maximum radius inscribed in the outline is set as the center of the palm. Next, in 405, the fingertips and crotches of fingers are detected from the outline of the hand and the center of the palm. A distance profile from the center of the palm to each point on the outline is calculated, points on the closed curve at which a curvature value of the distance profile takes a local maximum value and is larger than a predetermined value are detected as the fingertips, and positions at which the curvature value takes a local minimum are detected as the crotches of the fingers. In the case where one or more fingertips are detected in 406, it is determined that the object detected in 402 is a hand, and attitude detection of the hand or fingers is performed in 407. In the case where the fingertips cannot be detected in 406, the process returns to object detection of 402. In the attitude detection of the hand, an inclination angle of the palm in a three-dimensional space with respect to the image capturing plane of the distance sensor 4 and an attitude variation in the vicinity of the palm can be detected from the distance data in the vicinity of the palm described above. The positions of the fingers are determined as the positions of the fingertips and crotches of the fingers detected in 405, and a region of the fingers is detected as a region including the fingertip and the crotch of each finger. The attitude of the fingers can be detected as an attitude variation in a three-dimensional space such as bending and warping of the fingers from the distance data of the region of the fingers extending from the crotch positions of the fingers to the fingertips. An example of a specific flow of an authentication method after detecting the attitude of the hand or fingers in the authentication apparatus 2 of FIG. 1 is illustrated in a flowchart of FIG. 23. In 501, the user shows the hand above the opening portion 3 the opening portion 3 for authentication. In 502, the position, the region, and the attitude of each finger are detected. Then, in 503, coordinate conversion from the distance image of the distance sensor 4 to the blood-vessel image of the image capturing portion 11 is performed, and the position and region of each finger in the blood-vessel image are determined. In 504, the region of each finger in the blood-vessel image is cut out, and, in 505, normalization processing such as rotation correction and correction of distortion caused by a three-dimensional attitude variation is performed on an image of a cutout finger region on the basis of attitude detection of each finger. A blood-vessel feature such as a blood-vessel pattern and a feature point is extracted in 506 from a cutout image of plural fingers after rotation correction and distortion correction, and, in 507, is matched with feature information of plural fingers registered in the storage device 14 in advance, and a matching score is calculated for each finger of the hand shown by the user. In the case where a score obtained by integrating plural matching scores calculated in 508 exceeds a threshold value TH1, it is determined that the user is a registered person, and, in 509, the fact that the authentication has been successful is displayed on the display portion 16, and the loudspeaker 15 performs notification that the user has been authenticated via an electronic sound or a voice sound. In the case where the score is equal to or smaller than the threshold value TH1 and it is determined that the user is not a registered person, the fact that the authentication has been unsuccessful is displayed on the display portion 16 in 510, and the loudspeaker 15 performs notification that the authentication has been unsuccessful via a sound.

Fifth Exemplary Embodiment

In the present exemplary embodiment, authentication of a so-called walk-through type that utilizes blood vessels of fingers, particularly veins, in which the authentication apparatus of FIG. 1 is used and a walking user shows the hand for authentication without stopping will be described. To be noted, although an example related to an entrance/exit system is used for description, it goes without saying that another embodiment such as an automatic teller machine of a bank may be employed.

Figure 24:
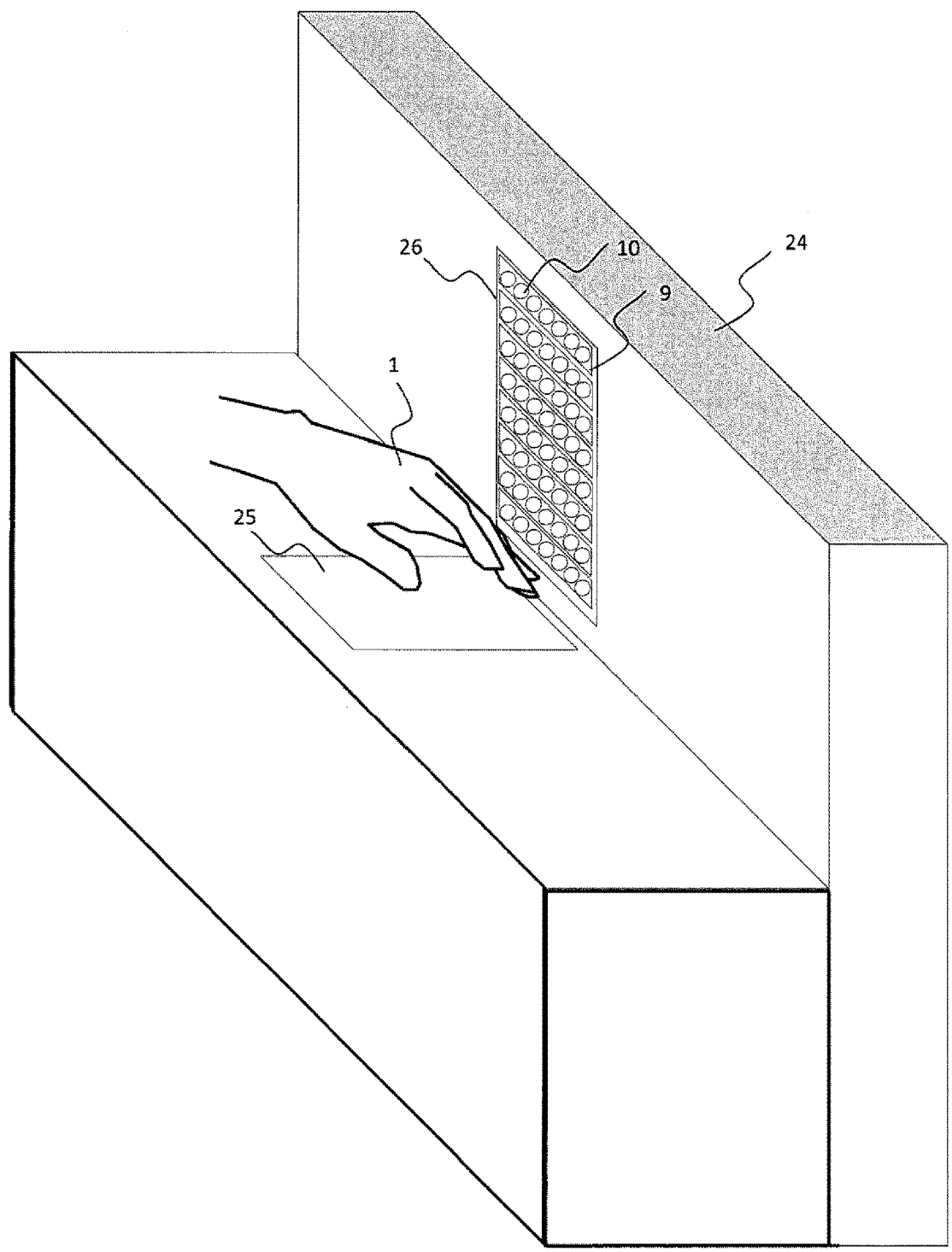
FIG. 24 is an example of a finger-blood-vessel authentication apparatus of a walk-through type.
Figure 25:
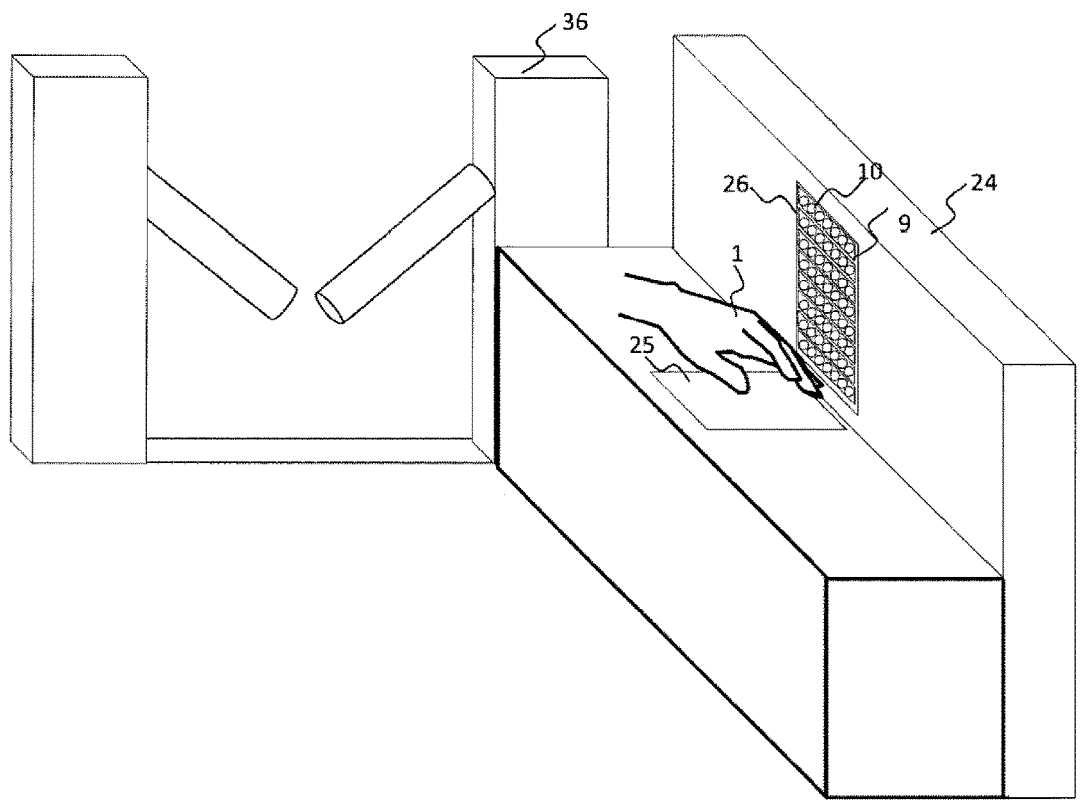
FIG. 25 is an example of the finger-blood-vessel authentication apparatus of a walk-through type integrally provided with an opening/closing gate.

To secure a path for the user to be authenticated to walk through, it is desirable that a configuration in which an exterior cover long in the moving direction of the user is attached to the outside of the authentication apparatus as illustrated in FIG. 24 such that time in which a moving hand is shown to the apparatus body becomes as long as possible is employed. An opening portion 25 corresponding to the opening portion 3 of the apparatus of FIG. 1 and an opening portion 26 corresponding to the opening portion 8 are provided in an exterior cover 24. As illustrated in FIG. 25, a system in which an opening/closing gate 36 is provided after the exterior cover 24, the opening/closing gate 36 opens when a walking user shows the hand and is authenticated, and the user can pass through the gate can be employed. To be noted, the opening/closing gate 36 may be in another form related to an entrance/exit system, for example, a door type such as an automatic door.

Since the user shows the hand while walking, the attitude variation of the hand is larger than the case where the hand is shown while standing still. Moreover, since the hand is shown while walking, the image capturing portion 11 is required to capture a blood-vessel image of fingers of a moving hand. However, in the case where the control of the light source array 9 does not keep up with the moving speed of the hand, a clear blood-vessel image of the fingers cannot be captured.

Therefore, a position at which the hand is to be shown is estimated in advance from the movement of the hand to be shown and lighting control of the light source array 9 is performed in advance. By radiating the point light sources 10, that is, the irradiation light source, at a timing at which the hand reaches an estimated position, a clear blood-vessel image of the fingers can be captured even in the case where the movement of the hand is fast. In other words, point light sources 10 arranged in the moving direction of the hand are selected as the irradiation light source.

If the movement direction of the user is restricted to one direction as illustrated in FIG. 24, the movement of the hand to be shown to the opening portion 25 will be restricted. For example, although the hand moves in the moving direction of the user, the possibility of the hand moving against the moving direction is low. Accordingly, a position to which the hand moves and a reaching time thereof can be estimated starting from the moment in which the distance sensor 4 or the image capturing portion 11 disposed below the opening portion 25 detects the hand, and the point light sources 10 for capturing a blood-vessel image of the fingers at an estimated position and an estimated timing can be turned on at the moment of showing the hand or immediately before the hand is shown.

Figure 26:
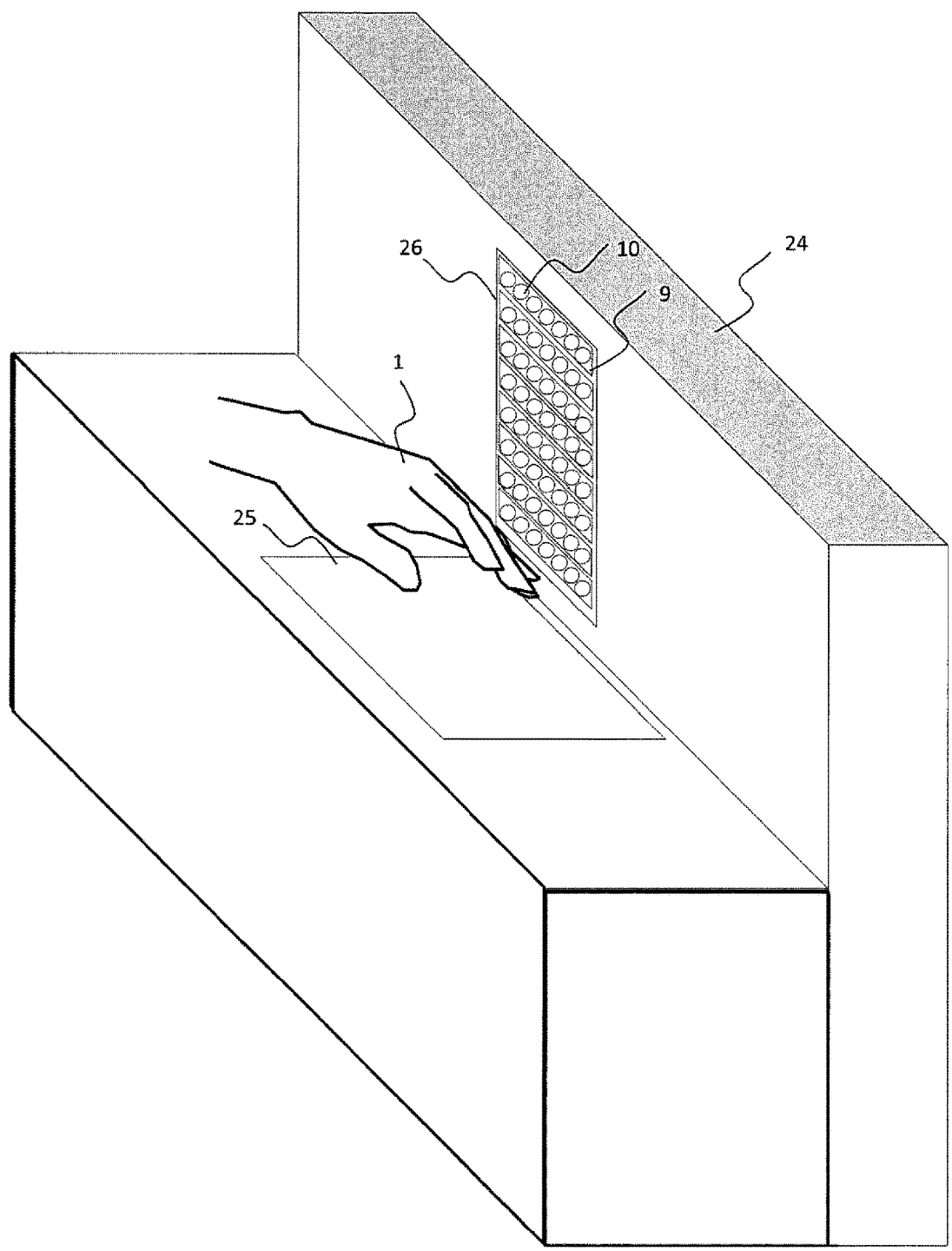
FIG. 26 is an example of the finger-blood-vessel authentication apparatus of a walk-through type with an opening portion extended in a moving direction of a user.

If the range of the opening portion 25 is narrow, a space or time for estimating the movement of the hand may be sometimes insufficient. Accordingly, the opening portion 25 of the exterior cover 24 is widened in the moving direction of the user and in the opposite direction thereof as illustrated in FIG. 26, and the movement of the hand is detected by the distance sensor 4 of FIG. 1 or an additional distance sensor that is not illustrated before the image capturing portion 11 captures a blood-vessel image of the fingers. At this time, the opening portion 3 of the authentication apparatus 2 corresponding to the opening portion 25 of the exterior cover 24 is also widened in the moving direction of the user and the opposite direction thereof. As a result of widening the opening portion 25, more space and time for detecting the movement of the hand can be secured than in the apparatus of FIG. 24, and it becomes easier to estimate the movement of the hand.

Figure 27A:
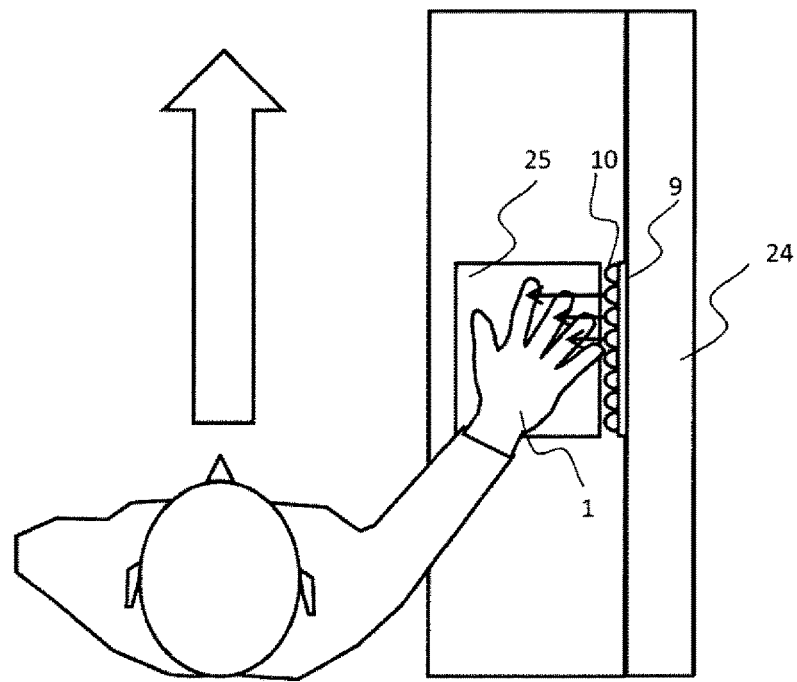
FIGS. 27A and 27B are examples of the attitude of the hand shown to the authentication apparatus of FIG. 24 by a walking user.
Figure 27B:
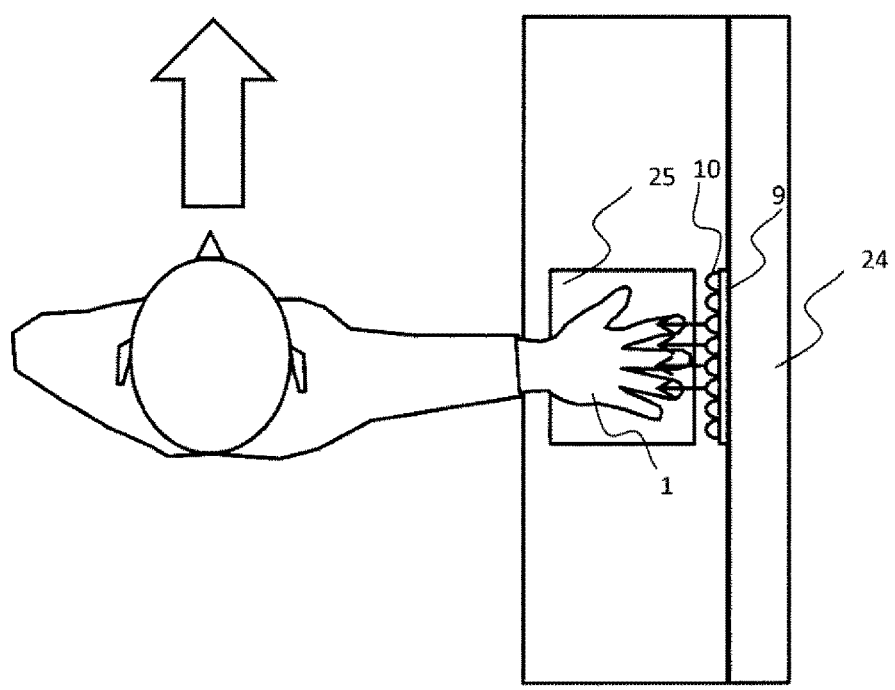
Figure 28:
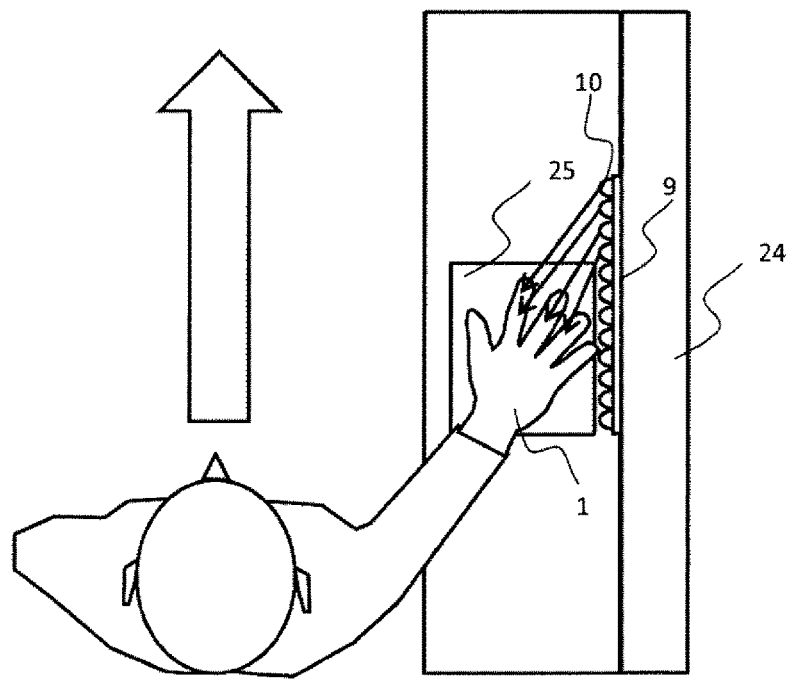
FIG. 28 is an example of light source arrangement for capturing a clear image of the blood vessels in the fingers of the hand shown while walking.
Figure 29:
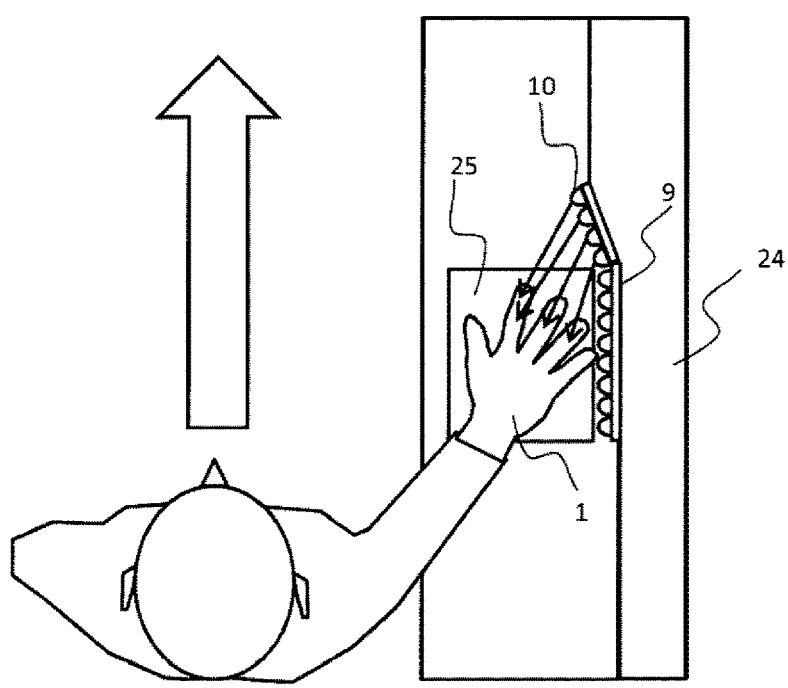
FIG. 29 is an example of light source arrangement for capturing a clear image of the blood vessels in the fingers of the hand shown while walking.

Since the time in which the walking user shows the hand to the authentication apparatus 2 is shorter than the time of showing the hand while standing still, and the showing attitude of the hand varies more greatly while walking, it is difficult to capture a clear blood-vessel image of the fingers. Further, in the case where the movement direction of the user is constant, not only the movement direction of the hand but also the attitude of the hand to be shown is restricted. For example, in the case where the user shows the hand while walking as illustrated in FIGS. 27(*a*) and 27(*b*), a case where the attitude of the hand is as illustrated in FIG. 27(*a*) and FIG. 27(*b*) can be considered. Accordingly, the irradiation angle and the arrangement of each point light source 10 of the light source array 9 are determined such that a clearer image of the blood vessels of the fingers can be captured with the attitude of the hand the user shows while walking. With the arrangement of the point light sources 10 of the light source array 9 of FIG. 3, (as described in the first exemplary embodiment) the irradiation light from the point light sources 10 is likely to pass through the fingers when the hand is shown with the attitude of FIG. 27(*b*), and a clear blood-vessel image can be captured. By contrast, since the irradiation light from the point light sources 10 is radiated onto the side surfaces of the fingers and is directly reflected and received by the image capturing portion 11 when the hand is shown with the attitude illustrated in FIG. 27(*a*), a brightness saturation region occurs on one half-side of the fingers in the blood-vessel image. Accordingly, the point light sources 10 of the light source array 9 are disposed so as to be displaced from the position of the opening portion 25 in the advancing direction of the movement direction of the user as illustrated in FIG. 28, and the irradiation angle of the point light sources 10 is adjusted such that the irradiation light from the point light sources 10 on the advancing side in the user movement direction in the light source array 9 is radiated onto the fingers of the hand with the attitude of FIG. 27(*a*). Specifically, it is desirable that the angle of the point light sources 10 serving as the irradiation light source has a shape more inclined towards the front side of the direction of the fingertips than other light sources. By radiating the light from the front of the fingertips as illustrated in FIG. 28, the irradiation light can be made less likely to be radiated onto the side surfaces of the fingers and the amount of light passing through the fingers can be increased, and thereby a clear blood-vessel image can be captured. Further, by adjusting the arrangement of the point light sources 10 of the light source array 9, a clearer image of the blood vessels of the fingers of the hand shown with the attitude of FIG. 27(*a*) is captured. By inclining (to a degree that does not hinder walking of the user) the point light sources 10 on the advancing side in the user movement direction of the light source array 9 towards the front side of the user movement direction as illustrated in FIG. 29, the amount of irradiation light with which the side surfaces of the fingers are irradiated can be further reduced, and the amount of light passing through the fingers can be increased.

In addition, a marking such as a handprint is provided on the opening portion 3 or the opening portion 25 to make it easier for a walking user to show the hand at a predetermined position. By using a material that transmits near infrared light and shields visible light for the marking, the position for showing the hand can be notified to the user without having a bad influence on image capturing of the blood vessels of the fingers.

Sixth Exemplary Embodiment

In the present exemplary embodiment, a method of performing identity verification more efficiently from the viewpoint of performing high-speed and highly precise authentication by also using device authentication in the finger-blood-vessel authentication of a walk-through type of the fifth exemplary embodiment will be described. According to the fifth exemplary embodiment that does not utilize device authentication, there is a case where the feature information extracted from a blood-vessel image of the fingers when the hand is shown to the apparatus of FIG. 24 and the blood-vessel image of the fingers is captured requires to be matched with all feature information stored in the storage device 14 to be authenticated. In the case where feature information of so many people is registered in the storage device 14, the time required for authentication becomes longer. In addition, since matching is performed with feature information of many strangers, the risk of occurrence of authentication error increases. However, by performing device authentication at the time of or immediately before showing the hand and performing only matching with biological feature information associated with an ID of the authentication device stored in the storage device 14 to perform authentication, it becomes possible to reduce unnecessary matching between different biological feature information and perform efficient and fast authentication. In other words, by performing biological authentication after specifying or narrowing down plural pieces of registered data by performing authentication between an ID associated with plural pieces of registered data stored in the storage device 14 in advance and an ID stored in another device before biological authentication, the number of pieces of registered data to be subjected to biological authentication can be reduced from the population of the whole of the plural pieces of registered data. Therefore, biological authentication can be completed in a shorter time than in the case of performing biological authentication using all combinations of all pieces of registered data.

Figure 30:
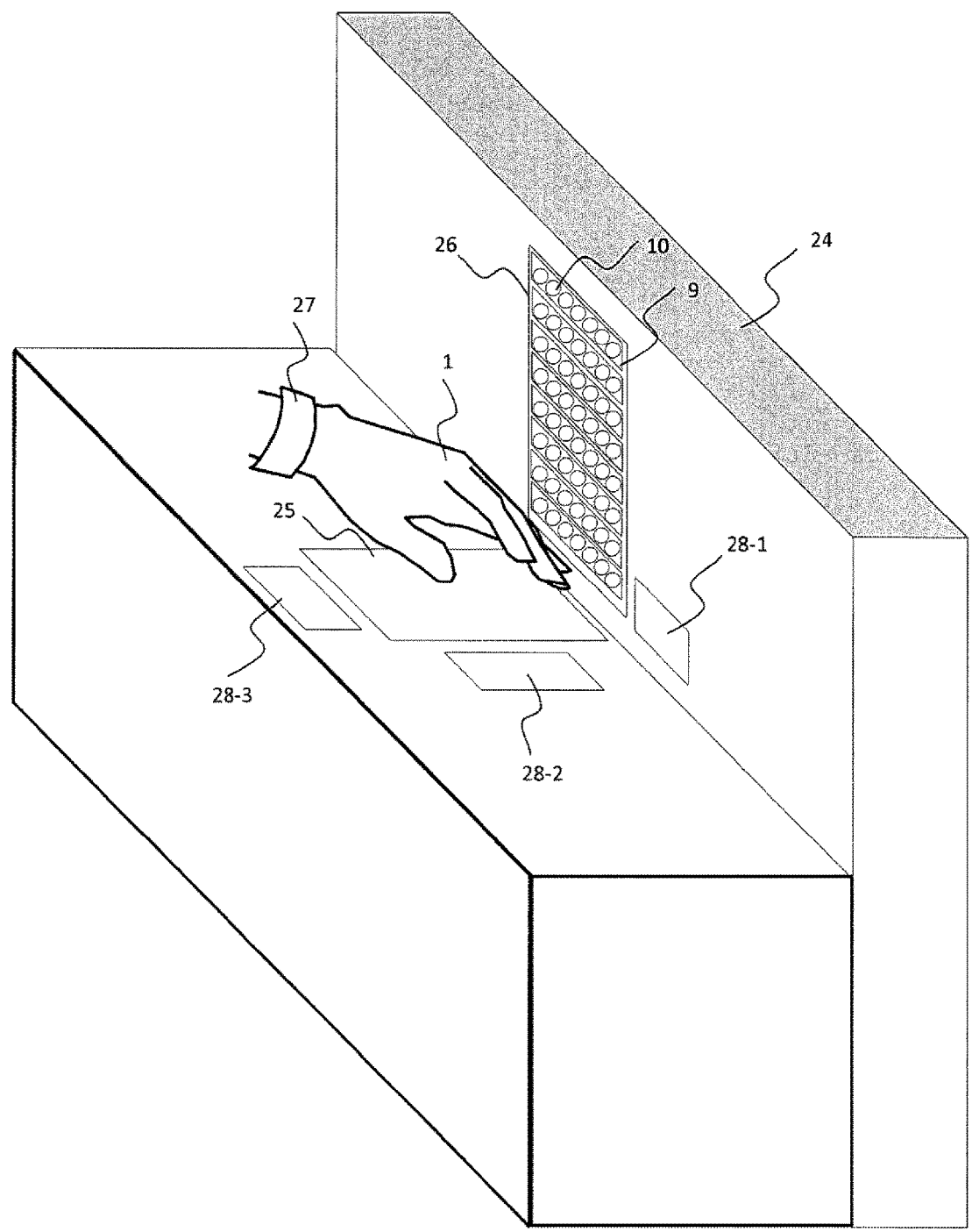
FIG. 30 is an example of a finger-blood-vessel authentication apparatus of a walk-through type that also utilizes device authentication.

In the present exemplary embodiment, an authentication method utilizing a watch type (wristband type) authentication device will be described as another example of device authentication. An authentication device of a type to be worn on an arm and the fingers that are a target of blood-vessel image capturing can be shown to the apparatus body with one movement because naturally the whole hand including the finger portion is shown to the apparatus body when showing the authentication device on the arm to the apparatus body for authentication. Therefore, the time for a series of operation from the user showing the hand (fingers and the arm) to the completion of authentication can be greatly shortened. According to an apparatus configuration illustrated in FIG. 30, an ID reading apparatus 28 is disposed in the vicinity of the opening portion 25 such that an authentication device 27 worn on the wrist comes close to the ID reading apparatus 28 when the user shows the hand at the opening portion 25 while walking and a blood-vessel image of the fingers is captured, and this enables performing device authentication and biological authentication using the blood vessels in the fingers at the same time. In the example of FIG. 30, an attitude variation of the time of showing the hand while walking is accepted. Thus, the reading terminal 28 is disposed such that the authentication device 27 at a wrist part of the hand can always read an ID from a short distance. A reading terminal 28-1 on the disposition plane side of the light source array 9 on the front side in the user movement direction, a reading terminal 28-2 in the vicinity of a showing portion 25 on the front side in the user movement direction, a reading terminal 28-3 on the opposite side to the light source array 9 when seen from the showing portion 25, and so forth can be disposed on the exterior cover 24 or embedded in the exterior cover 24. Of course, a method in which a receiving portion (antenna or the like) of an ID reading terminal is disposed as described above and the body of the terminal is disposed on another board inside the apparatus body may be employed.

In addition, a configuration in which a showing position of the palm or the fingers is marked to guide the hand shown by the user to a predetermined position, the fingers are shown above the opening portion, and the arm is shown above the terminal 28 with one movement can be employed to cause the ID of the authentication device 27 of the watch type to be read quickly and easily.

Figure 32:
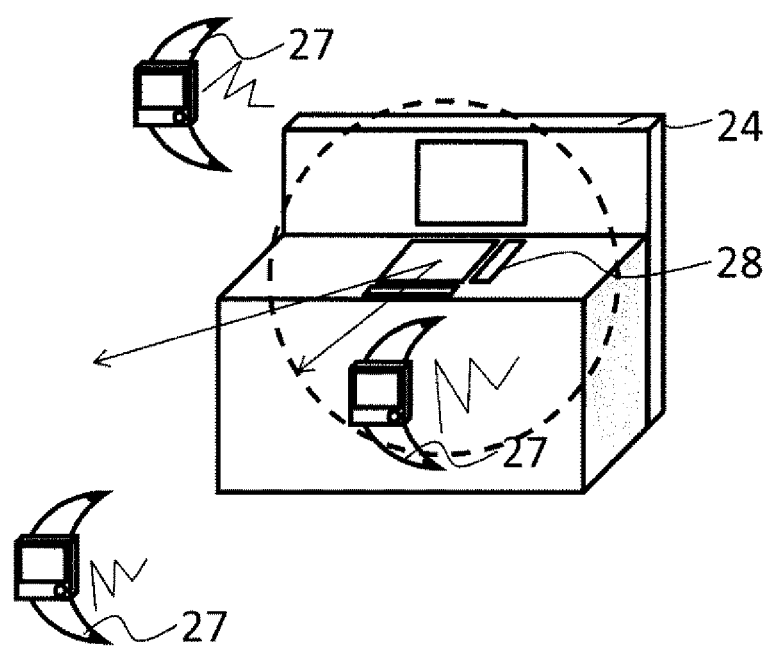
FIG. 32 is an explanatory diagram of a method for detecting a specific authentication device from plural authentication devices.

In the example described above, application of a device authentication means of a proximity type has been considered. However, in the case of a terminal of a watch type, it is possible that the terminal is worn on the other hand than the hand to be used for authentication, a case where the ID cannot be read properly can be considered. Alternatively, it can be considered that the authentication device 27 is configured as a neck-holder type that is hung from the neck or a miniature type that can be put in a pocket. Wearable terminals are often designed on the premise that communication is performed with a smartphone and the like serving as a mother ship, and many of these have a radio-wave communication function. These communication functions typically include a function called received signal strength indicator (RSSI) that monitors a radio wave condition all times, and the intensity of a radio wave at the time of a communication partner sending a signal can be easily known. When a device performs transmission with the same output, RSSI generally has a tendency of becoming stronger as the distance is shorter. Accordingly, in an environment in which the output is equalized, the authentication device 27 positioned closest to an authentication apparatus 24 can be found from plural authentication devices 27 by examining an RSSI value from the ID reading portion of the present invention as illustrated in FIG. 32. Then, by performing authentication by using registered biological data associated with an ID transmitted by the terminal, authentication can be performed without any problem even in the case where the authentication device 27 is on the opposite side of the hand and other terminals of the same type are present nearby. In this case, it is no longer required to guide the position of the hand of the user or take care to cause the authentication device 27 and the ID reading terminal to be close to each other. However, in the case where the authentication device 27 is somehow shielded or a shielding object is present between the authentication device 27 and the authentication apparatus of the present invention, the RSSI value becomes low and a similar device present in a distant position may sometimes indicate a higher RSSI value. Therefore, when performing authentication, a target range of radio-wave intensity is expanded, all IDs of authentication devices 27 having a radio-wave intensity of a predetermined value or more are checked, all-combination matching (1:N matching) is performed between all of found IDs and registered biological data associated therewith, and it is determined that the authentication has been successful if there is a match. By expanding the target range of radio-wave intensity, the distance from the position at which the hand is shown for authentication is increased. Thus, the system can catch the authentication device 27 at an early time point at which the user is approaching when performing walk-through authentication, and an ID to be set as an authentication target can be obtained. Even in the case where registered biological data is not present in the apparatus body of the authentication apparatus but is kept on a server connected thereto via a network or stored in the authentication device 27 and there is no need to call the registered biological data, communication can be performed before the user reaches an authentication position, and stress-free authentication can be provided. According to the method described here, 1:N matching is performed with plural IDs. However, compared with a case where thousands of registered users are present and 1:N matching is performed with all of these, the present method that can limit N to several IDs is an effective method also in view of ensuring the precision.

Figure 33:
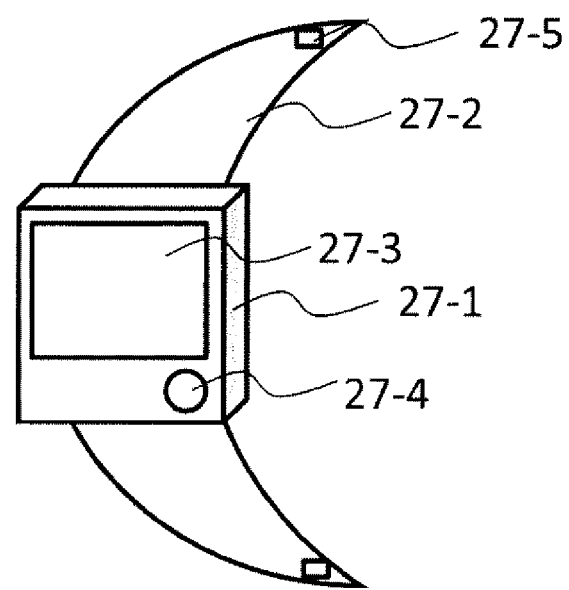
FIG. 33 is an example of a wristband-shaped authentication device.

FIG. 33 illustrates a specific example of the authentication device 27 of a wristband type used in the exemplary embodiment described above. The authentication device 27 is constituted by a body portion 27-1 and a band portion 27-2, and sometimes includes a display 27-3 for displaying information. The display 27-3 can include a touch panel interface. The authentication device 27 has a radio-wave communication function as described above, and is capable of performing mutual communication with an external device. If setting is performed in advance, the device 27 can transmit a device ID in response to a request for transmission data or the like from the ID reading terminal 28. The user can arbitrarily designate whether transmission may be performed via settings for the device 27. In addition, by displaying a message or the like requesting an ID transmission permission on the display 27-3 and providing an interface for confirmation, the user can know that an request for ID transmission has been made by the authentication apparatus, and thereby the security can be improved. When authentication is performed at the authentication apparatus 24, the results thereof can be received and also displayed on the display 27-3.

In particular, in the case where the authentication has been successful, an inner state of the authentication device 27 can be caused to transition to another state. The authentication having been successful means that identity verification of the user wearing the authentication device 27 has been strictly performed through biological authentication. Generally, a device has a risk of, for example, being stolen and used by a person who is not the owner. This is because being worn does not necessarily mean that the device is used by an official owner. Therefore, imparting the wearable terminal itself with a biological authentication function and not allowing the use described above except in an inner state in which the authentication has been successful. However, it is technically difficult to imparting a biological authentication function into a very small terminal, and there has been a problem such as the precision being insufficient or the wearable terminal being required to be enlarged. However, if the authentication result of the authentication apparatus 24 is safely reflected on the authentication device 27, the above problem will be solved. In particular, since the authentication apparatus 24 is capable of performing authentication that is robust against the attitude variation of the hand and quick, the authentication apparatus 24 can be used with a high precision without being skillful compared with common biological authentication, and there is also a merit that it becomes easier to utilize biological authentication. Therefore, the inner state of the authentication device 27 is caused to transition and functions such as payment and use as a substitute key are allowed to be used only in the case where authentication has been successfully performed by the authentication apparatus 24. When the transition is performed, an indicator lamp 27-4 illustrated in FIG. 33 is turned on, and the user is notified that usage for the various uses described above is now available. Of course, this can be substituted by displaying a similar mark on the display 27-3. However, in the case where the device is stolen in the transition state, the damage cannot be prevented any longer. Therefore, the transition is performed only when the band firmly keeps a ring shape and the authentication device 27 is in a state not likely to slip off the hand, and a function of forcibly terminating the transition when the ring comes off is provided. Whether a ring shape is kept can be determined by, for example, providing a contact switch 27-5 and determining whether it is electrically connected. Further, as a method for improving the security, the above-described worn/not worn confirmation of the authentication device can be performed after confirming that the authentication device 27 is worn by a living body by providing a biological sensor in the authentication device 27 and checking the pulse of a blood flow and the presence of heartbeat.

Figure 34:
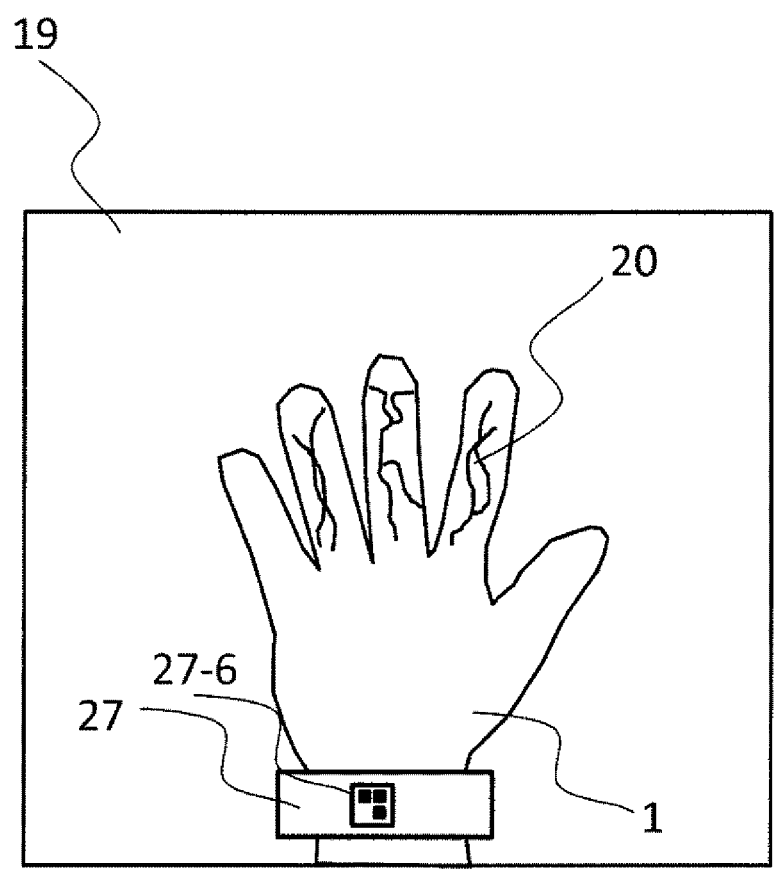
FIG. 34 is an example of a case of reading an authentication code by a finger-blood-vessel image capturing portion.

Although a method of utilizing a terminal of a radio-wave communication type has been described above, such an electronic terminal takes certain costs. Therefore, printing an identification mark such as a barcode on a wristband and utilizing the barcode can be also considered as a method of obtaining an ID at a lower cost. FIG. 34 illustrates an example of an image capturing screen during authentication, and a wristband is wrapped around an arm. A barcode or a two-dimensional code is printed on the wristband, and an ID is obtained by reading the code in the image capturing screen during authentication. Further, by using the obtained ID as described above, 1:1 authentication can be realized. The printed barcode is set such that an image of the barcode can be captured at any position by, for example, redundantly printing the barcode on plural positions such that the barcode does not disappear from the angle of view of the image capturing screen during authentication as a result of the wristband rotating on an upper arm.

Seventh Exemplary Embodiment

In the present exemplary embodiment, a method of registering plural finger-blood-vessel features obtained by the authentication apparatus 2 of the first exemplary embodiment for realizing a highly precise finger-blood-vessel authentication will be described. Since the authentication apparatus 2 can obtain blood-vessel features of plural fingers at the same time, an ID of an registered person can be registered in association with the blood-vessel features of plural fingers. To perform highly precise authentication, blood-vessel features of plural fingers can be registered by using a blood-vessel image of a moment in which a clear image of blood vessels of all the fingers is captured. In the case where a clear image of the blood vessels of all the fingers cannot be captured at the same time, a registration processing period can be provided, and the blood-vessel features can be registered for images of respective moments in which clear images of blood vessels of respective fingers are captured in images captured during the period. In this registration processing period, guidance information of an attitude of the hand in which a registered person should show the hand can be displayed on the display portion 16, and a sound guidance can be performed by using the loudspeaker 15.

If the attitude variation of the hand or fingers is large, a lighting condition by the irradiation light of the light source array 9 also changes. Therefore, when only blood-vessel features from an image captured with one showing attitude of the hand are registered, it can be considered that various attitude variation cannot be addressed. Accordingly, by registering blood-vessel features from images captured with plural attitudes of the hand or fingers, it becomes possible to perform authentication with various showing attitudes of the hand.

To prevent registration of a forged artificial article, gesture recognition of the shown hand is performed at the time of registration, and a forged article (artificial article) such as a rigid body is rejected by causing a registered person to perform a designated gesture.

Eighth Exemplary Embodiment

In the present exemplary embodiment, an example of an authentication method using plural finger-blood-vessel features obtained by the authentication apparatus 2 of the first exemplary embodiment will be described. By not only simply using plural finger-blood-vessel features but also using a limiting condition such as a spatial arrangement order of fingers, matching of blood-vessel features is performed efficiently, and thereby highly precise authentication is realized.

An outline of the authentication is as follows. Matching between blood-vessel features of plural fingers obtained by the authentication apparatus 2 and blood-vessel features of plural fingers collectively stored in the storage device 14 for each ID is performed, matching results of blood-vessel features of respective fingers are integrated, and authentication is performed on the basis of the integrated matching score. To be noted, configurations, operations, and processes similar to the exemplary embodiments described above will be omitted.

Figure 35:
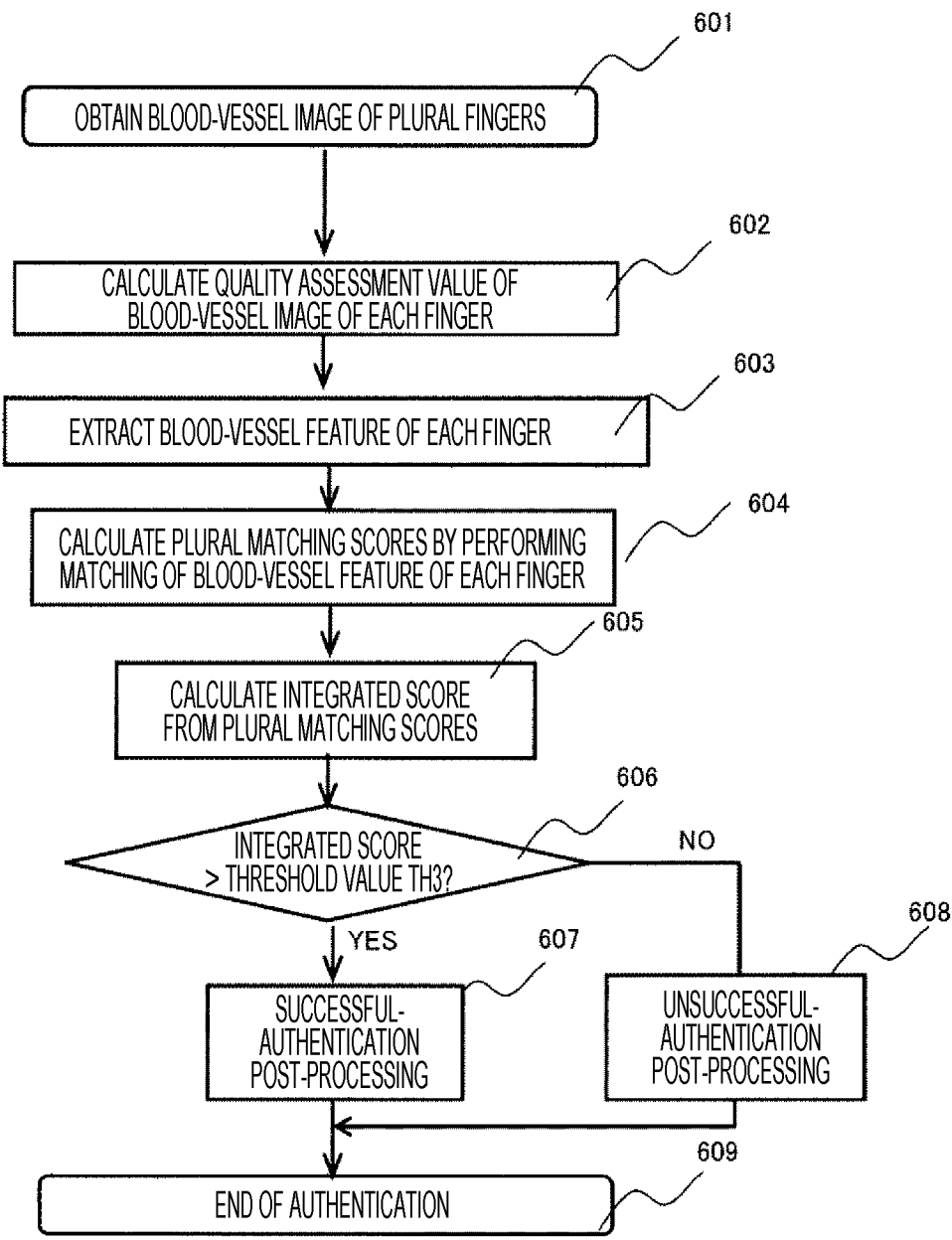
FIG. 35 is an example of a flowchart of authentication using matching of plural blood-vessel images of fingers.

FIG. 35 illustrates an example of a flowchart of performing authentication processing using a blood-vessel image of plural fingers. First, a blood-vessel image of plural fingers is obtained in 601, a quality assessment value of a blood-vessel image is calculated for each finger in 602, and a blood-vessel feature of each finger is extracted in 603. Each extracted blood-vessel feature is subjected to matching in 604, and a matching score is calculated for each blood-vessel feature. In 605, one integrated score is obtained by combining plural matching scores. Whether the integrated score exceeds a preset threshold value TH3 is determined in 606. In the case where the integrated score exceeds the threshold value TH3, successful-authentication post-processing is performed in 607, and, in the case where the integrated score is lower than the threshold value, unsuccessful-authentication post-processing is performed in 608. To be noted, the quality assessment value of 602 does not need to be calculated.

As to an authentication method utilizing a matching score of plural blood-vessel features, there is a method in which one integrated score is obtained by combining two or more plural scores and authentication is determined to be successful when the integrated score exceeds a preset threshold value TH3. As the matching scores used for generating the integrated score, matching scores of blood-vessel features with high quality assessment values can be prioritizedly selected on the basis of, for example, an index (quality assessment value) indicating whether a clear image of the blood vessels is obtained in the blood-vessel features and the blood-vessel image obtained in 602 of the flowchart of FIG.

35. In addition, there are a method in which authentication is determined to be successful when one or more matching scores in plural matching scores exceed a preset threshold value TH2 and a method in which authentication is determined to be successful when at least N matching scores (N>1) exceed the threshold value TH2.

Due to a restriction in the showing attitude of the hand and due to a restriction in the arrangement of the light source array 9, there may be a finger whose clear blood-vessel image can be obtained and a finger whose clear blood-vessel image cannot be obtained, depending on the attitude of the hand shown at the time of input. In the case where there are a finger whose clear blood-vessel image can be obtained easily and a finger whose clear blood-vessel image cannot be obtained easily depending not on individual differences of living bodies but on the showing attitude of the hand and the configuration of the authentication apparatus 2, erroneous authentication can be suppressed and highly precise authentication that more reflects results in which identical fingers coincide can be realized by setting a larger weight for a matching score of a finger whose blood-vessel image is easier to capture and a smaller weight for a matching score of a finger whose blood-vessel image is more difficult to capture in matching scores of blood-vessel features of plural fingers.

Figure 31:
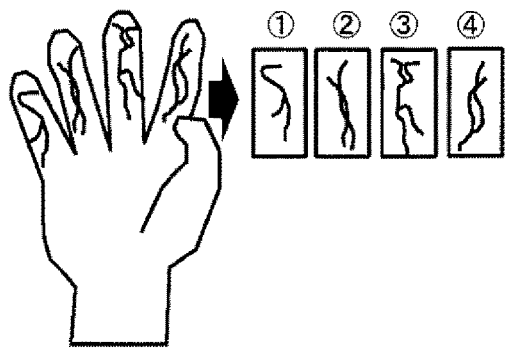
FIG. 31 is an example of a matching method of blood-vessel features using a sequential relationship between fingers.
Figure 31:
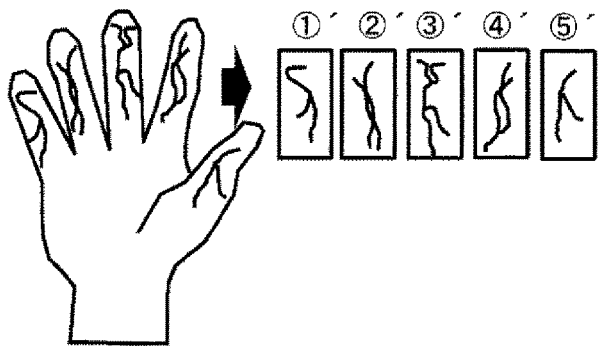
Figure 31:
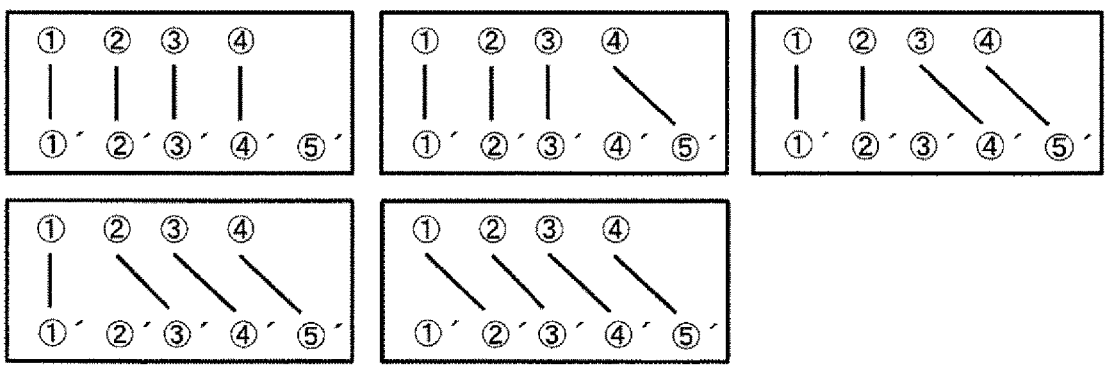

Next, an efficient matching method of plural finger-blood-vessel features using a spatial arrangement order of fingers will be described. For example, in the case where four fingers of the shown hand is detected and four finger-blood-vessel features are input, a case where the input is matched with five finger-blood-vessel features of a certain registered ID is considered. Since the input number of fingers does not match the registered number of fingers, correspondence between fingers cannot be grasped. However, if the input finger-blood-vessel features and the registered finger-blood-vessel features are subjected to matching in an all-combination manner, the number of times of matching between different fingers, which are naturally not to be subjected to matching, increases. To address this, matching is performed with the registered five finger-blood-vessel features while keeping the spatial arrangement order of the four detected fingers. Accordingly, since an unnecessary number of matching can be cut by removing matching of plural fingers that are different from the actual arrangement of fingers as illustrated in FIG. 31, authentication can be performed more quickly and at a higher precision.

Ninth Exemplary Embodiment

In the exemplary embodiments described above, a means for expanding a restriction range of showing attitude in the configuration employing a light source array projecting to the side of an opening portion has been described. In the present exemplary embodiment, a means for permitting an image capturing restriction range by the showing attitude of the fingers will be described as another exemplary embodiment of the apparatus.

Figure 36:
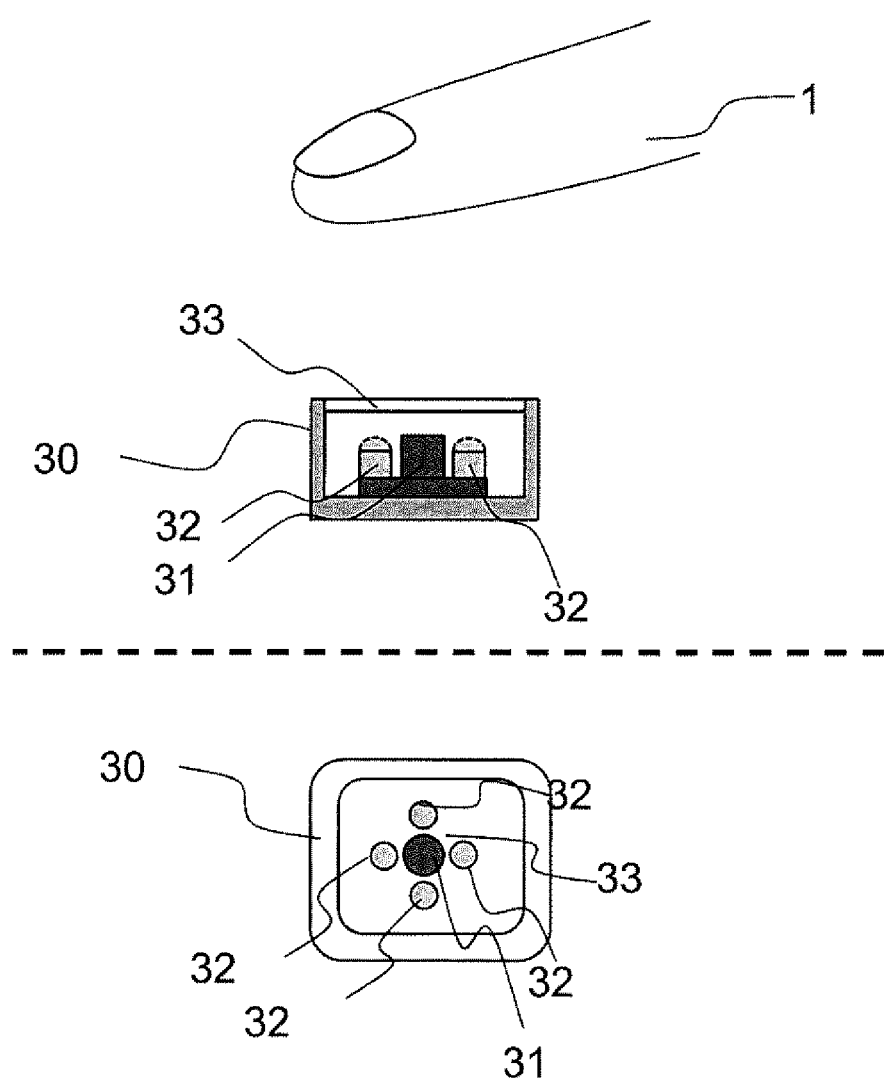
FIG. 36 is an example of an overall configuration of a biological authentication apparatus using biological information of a finger and capable of authenticating without contact.

FIG. 36 illustrates an overall configuration of a biological authentication apparatus using biological information of fingers and capable of authenticating without contact.

A camera 31 and light sources 32 around the camera 31 are provided inside an authentication apparatus 30, and the light sources 32 radiate visible light or light including a wavelength region of infrared light toward a finger 1. The camera 31 has a light-receiving sensitivity to the wavelength region of the light radiated from the light sources 32, and captures an image of reflection light that reflects the finger 1 or scattering reflection light (subsurface scattering light) that is emitted from the finger 1 again after being once absorbed by the finger 1. An optical filter 33 is provided in the optical axis direction of the camera 31, and has an effect of transmitting only the wavelength region of the light radiated from the light sources 32. To be noted, although four light sources are provided in the present exemplary embodiment, the number may be one or greater as long as the finger 1 is irradiated with light.

After the authentication apparatus 30 starts operating, the light sources 32 first quickly switches between lighting and not lighting, and the camera 31 captures an image thereof. If the finger 1 serving as an object approaches the authentication apparatus 30, the light radiated from the light sources 32 reaches the finger 1, and thus the finger 1 is observed to be blinking in accordance with blinking of the light sources 32. In the case where the variation of the average value of brightness value changing in the blinking is equal to or larger than a certain value and the number of pixels satisfying this condition is greater than a certain number, it is regarded as approach of the finger 1 and authentication processing is started.

To be noted, polarization filters may be provided in the optical axes of the light sources 32 and the camera 31. By displacing the polarization axis of the polarization filter attached to the light sources 32 and the polarization axis of the polarization filter attached to the camera 31 by 90 degrees, mirror reflection light that is a light component reflected on the surface of the finger 1 can be removed. Therefore, a clearer image of blood vessels inside the fingers can be captured in this case. In addition, a mirror reflection component and a scattering reflection component may be respectively captured by causing two light sources to coincide with the polarization axis of the camera 31, causing the other two light sources to be perpendicular thereto, and alternatingly turning the respective two light sources on to make use of the fact that plural light sources 32 are provided. At this time, since fingerprint information of the surface of the finger and blood-vessel information of inside of the finger can be captured independently, biological information of a high image quality can be obtained.

Figure 37:
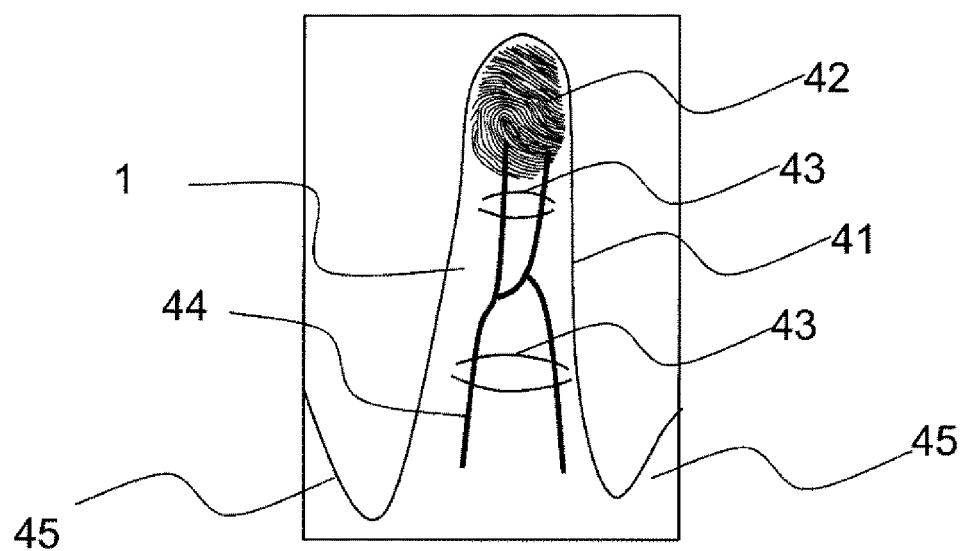
FIG. 37 is an example of a finger image captured in a ninth exemplary embodiment.

FIG. 37 is an example of a picture of the finger 1 captured by the authentication apparatus 30. The picture includes an outline 41, a fingerprint 42, joint wrinkles 43, and blood vessels 44 of the finger 1. Further, an image of a part 45 of an adjacent finger is simultaneously captured.

First, the outline 41 of the finger 1 is detected via a general method such as contour tracing or graph cut, and an inside region and an outside region of the finger 1 are distinguished. At this time, a borderline therebetween is obtained as a finger outline. At this time, a difference between two images of lighting and non-lighting of the light sources may be obtained. As a result of this, unnecessary objects other than the finger and external light are efficiently removed, and a finger region can be stably derived. Next, an average vector is obtained by regarding the finger outline as a vector. As a result of this, the longitudinal direction of the finger is obtained. Next, information about a fingertip position and a root position of the finger is obtained. This can be obtained by detecting a part of the finger outline with a large curvature. Then, the direction and magnification of the finger are normalized by using the position information of the fingertip and the root of the finger. As a result of processing up to this point, attitude information of the captured finger can be obtained. At this time, as described in the exemplary embodiments described above, it becomes possible to improve the image quality by adjusting the intensity of each of the plural light sources 32 in accordance with the attitude information of the finger.

Finally, the fingerprint, the wrinkles of the joints of the finger, and the blood vessels are obtained from a normalized finger image. Since the fingerprint includes a fine pattern, the fingerprint is obtained by using a spatial filter that emphasizes a high-frequency component matching the pitch of the fingerprint. In addition, the wrinkles of the joints of the finger are obtained by using a spatial filter that emphasizes lines perpendicular to the direction of the finger. Similarly, the blood vessels are obtained by using a spatial filter that emphasizes lines parallel to the direction of the finger. To be noted, as to image capturing of the blood vessels, images of two wavelengths may be captured by using arbitrary two of the four light sources 32 shown in the present invention as elements that radiate different wavelengths, and the blood vessels may be obtained from the brightness that changes in accordance with a difference in absorbance of blood vessels of infrared light. According to this method, a precise blood-vessel pattern can be obtained.

By using one or more pieces of biological information extracted in this way, non-contact biological authentication using biological features can be realized regardless of the showing attitude even if the finger and the apparatus are not in contact.

To be noted, to guide a position at which the finger is to be placed, a picture of the finger may be shown on the display, and information that guides the finger position via sentences and drawings may be shown. The user can adjust the finger position by looking at this information, and thereby the precision of authentication can be improved. To be noted, since the direction in which the finger is shown can be automatically corrected, guidance that guides only the distance between the finger 1 and the authentication apparatus 30 may be alternatively employed. As a result of this, it becomes possible to show a guide that is more convenient for the user. Alternatively, an operation method in which the finger 1 is first caused to contact the authentication apparatus 30 and then slowly moved away may be employed, and an image for authentication may be obtained at an appropriate timing while continuously performing image capturing until the magnification of the finger becomes a certain region. This can suppress a large positional displacement of the finger, and thus precision and usability can be achieved simultaneously.

An exemplary embodiment of application software that switches specific functions in accordance with the position of the finger will be described below. In the authentication apparatus described above, when a captured portion of the finger 1 is changed, biological information captured in that range is also changed. For example, when the biological information of the fingertip, an intermediate portion (middle joint portion) of the finger, and the root of the finger are each registered in advance and each part is shown, similarity to each piece of registered data increases, and thus functions defined by application software can be assigned on the basis of the matching results. Alternatively, an image of a wide range of the finger may be captured and registered in advance, a degree of positional displacement may be obtained by calculating how much the position of the finger is displaced from a registered state, and the functions may be assigned on the basis of the results of this.

In the case where the application software is a video game, movements of a character controlled by the user themselves are defined in advance as functions, and each movement is generally changed in accordance with the kind of buttons of a game controller. For example, movements such as run, jump, and squat are assigned to an A button, a B button, an X button, and the like, and predetermined movements are performed by the user pressing these buttons. Meanwhile, it is possible to assign a movement to each finger, for example, it is possible to perform assignment such that the character runs when an index finger is shown, jumps when a middle finger is shown, and the like. Similarly, a function may be assigned to each of the fingertip, the middle joint portion, and the root of the same finger.

In the case where the application software is a video game of throwing a javelin, a function of giving a run-up, a function of adjusting a throwing angle of the javelin, and the like may be freely assigned to specific portions of the finger. The character is caused to give a run-up by showing a finger for the run-up, a finger for adjusting the throwing angle is shown at a matching timing when the character reaches a takeoff plank, and the javelin is thrown when the finger is moved away at a matching timing. At this time, the flying distance is determined in accordance with the speed of the run-up and the throwing angle. The speed of the run-up may be configured to become faster when the similarity to registered biological information is higher. In addition, plural portions of a living body may be assigned with the run-up function, and it may be configured that the speed of the run-up becomes faster by quickly showing these portions in an alternating manner.

This can be applied not only to the movement of the character but also to an application for playing the instruments such as a piano and a drum. For example, notes or the types of the drum may be changed in accordance with an image capturing position of the finger. In addition, it becomes possible to express various tones by smoothly changing the notes in accordance with the amount of displacement of the finger.

In addition, a blood concentration or an oxygen saturation concentration may be measured on the basis of the width of the blood vessels captured in an image or infrared light of plural wavelengths, and a characteristic of a game character may be changed in accordance with the results thereof. For example, a life value or an attack value of a character may be increased for a user with a high blood concentration. Alternatively, a blood pulse may be detected, and a characteristic of speed may be lowered and a frequency of the attack value getting doubled in a certain possibility may be increased in the case where the blood pulse is shallow and fast. In addition, the type of tools that can be equipped by the character or the type of spells that can be used by the character may be changed in accordance with the value of the oxygen saturation concentration. Similarly, as a game of fighting an enemy, an attack is made by showing a living body. At this time, a fighting game in which more life of an opponent can be taken as the living body is shown as a better reproduction can be realized by employing a configuration in which the own attack value becomes higher as the similarity between an own registered pattern and an input pattern is higher.

As described above, by measuring the degree of reproduction or similarity of the living body between the time of registration and input, the health condition of the user, or the like and reflecting that information on the game character, a game application with a more realistic feel can be provided.

To give a part of solutions described in the first exemplary embodiment and subsequent embodiments described above as an example, the part of solutions are as follows.

Configuration 1: A blood-vessel image capturing apparatus including an opening portion formed in a surface of a housing, plural light sources disposed beside the opening portion and arranged in a lattice pattern, a sensor configured to obtain position information of a hand shown above the opening portion, a light amount control portion configured to select an irradiation light source to irradiate the hand from the plural light sources on a basis of the position information and control a light amount of the irradiation light source, and an image capturing portion configured to capture an image of a blood vessel included in a finger portion of the hand irradiated with light from the irradiation light source.

Configuration 2: The blood-vessel image capturing apparatus according to configuration 1, wherein the light amount control portion selects a light source that irradiates a root side of the finger portion as the irradiation light source from the plural light sources on the basis of the position information.

Configuration 3: The blood-vessel image capturing apparatus according to configuration 1 or 2, wherein a wavelength of light radiated from the sensor is different from a wavelength of light radiated from the plural light sources.

Configuration 4: The blood-vessel image capturing apparatus according to anyone of configurations 1 to 3, wherein, among the plural light sources, an acute angle made by an opening plane of the opening portion and an optical axis of a light source is smaller for the light source positioned from the opening portion by a smaller distance than the other light sources.

Configuration 5: The blood-vessel image capturing apparatus according to anyone of configurations 1 to 4, wherein, in a case where a blood-vessel region image included in the image includes a saturated region to a predetermined degree or more, the light amount control portion selects a light source positioned from the opening portion by a longer distance than the irradiation light source as a new irradiation light source.

Configuration 6: The blood-vessel image capturing apparatus according to anyone of configurations 1 to 6, wherein the position information is information based on a three-dimensional shape of the hand shown at the opening portion, and the light amount control portion controls the light amount of the irradiation light source in accordance with a length of a distance from the irradiation light source to the hand irradiated by the irradiation light source.

Configuration 7: The blood-vessel image capturing apparatus according to anyone of configurations 1 to 6, wherein the light amount control portion selects the light source disposed further on a moving direction side than the hand with respect to the moving direction of the hand moving above the opening portion as the irradiation light source.

Configuration 8: The blood-vessel image capturing apparatus according to anyone of configurations 1 to 7, wherein the blood-vessel image capturing apparatus calculates, on a basis of information obtained from the sensor, a center position of the hand and a direction of the finger portion with respect to the center position in an image of a region of the hand included in the image, and calculates a rotation angle of the hand.

Configuration 9: The blood-vessel image capturing apparatus according to anyone of configurations 1 to 8, wherein the plural light sources are disposed at positions out of a detection range of the sensor and an image capturing range of the image capturing portion.

Configuration 10: The blood-vessel image capturing apparatus according to anyone of configurations 1 to 9, wherein the sensor is disposed at such a position that a distance from the sensor to a center of the opening portion is longer than a distance from the plural light sources to the center of the opening portion.

Configuration 11: The blood-vessel image capturing apparatus according to any one of configurations 1 to 10, further including, on the surface of the housing, a reading portion configured to receive personal information from a terminal attachable to a wrist.

Configuration 12: The blood-vessel image capturing apparatus according to any one of configurations 1 to 11, wherein the blood-vessel image capturing apparatus transmits the image to an authentication portion that executes authentication of an individual.

Configuration 13: An individual authentication system including a terminal including an opening portion formed in a surface of a housing, plural light sources disposed beside the opening portion and arranged in a lattice pattern, a sensor configured to obtain position information of a hand shown above the opening portion, a light amount control portion configured to select an irradiation light source to irradiate the hand from the plural light sources on a basis of the position information and control a light amount of the irradiation light source, and an image capturing portion configured to capture an image of a blood vessel included in a finger portion of the hand irradiated with light from the irradiation light source, an authentication portion configured to obtain the image from the terminal and execute authentication of an individual, and a gate portion configured to open and close on a basis of information from the authentication portion.

Configuration 14: The individual authentication system according to configuration 13, wherein the light amount control portion selects a light source that irradiates a root side of the finger portion as the irradiation light source from the plural light sources on the basis of the position information.

Configuration 15: The individual authentication system according to configuration 13 or 14, wherein a wavelength of light radiated from the sensor is different from a wavelength of light radiated from the plural light sources.

REFERENCE SIGNS LIST 1 hand
2 authentication apparatus
3 opening portion
4 distance sensor
5 computer
6 memory
7 CPU
8 opening portion
9 light source array
10 point light source
11 image capturing portion
12 optical filter
13 interface
14 storage device
15 loudspeaker
16 display portion
17 visible light source
18 keyboard
19 blood-vessel image
20 blood vessel
21 brightness saturation region
22 angle of view of image capturing portion
23 angle of view of distance sensor
24 exterior cover
25 opening portion
26 opening portion
27 authentication device
28 authentication device reading terminal
30 authentication apparatus 31 camera
32 light source
33 optical filter
34 distance image
35 setting range of distance unmeasurable point
36 opening/closing gate
41 finger outline
42 fingerprint
43 wrinkle of finger joint
44 blood vessel
45 adjacent finger
50 data input portion
51 light amount control portion
52 image input portion

The invention claimed is:

1. A blood-vessel image capturing apparatus comprising:
an opening portion formed in a surface of a housing;
plural light sources disposed beside the opening portion and arranged in a lattice pattern;
a sensor configured to obtain position information of a hand shown above the opening portion;
a light amount control portion configured to select an irradiation light source to irradiate the hand from the plural light sources on a basis of the position information and control a light amount of the irradiation light source; and
an image capturing portion configured to capture an image of a blood vessel included in a finger portion of the hand irradiated with light from the irradiation light source;
wherein the light amount control portion selects a light source that irradiates a root side of the finger portion as the irradiation light source from the plural light sources on the basis of the position information; and
wherein, among the plural light sources, an acute angle made by an opening plane of the opening portion and an optical axis of a light source is smaller for the light source positioned from the opening portion by a smaller distance than the other light sources.

2. The blood-vessel image capturing apparatus according to claim 1, wherein, in a case where a blood-vessel region image included in the image includes a saturated region to a predetermined degree or more, the light amount control portion selects a light source positioned from the opening portion by a longer distance than the irradiation light source as a new irradiation light source.

3. The blood-vessel image capturing apparatus according to claim 2, wherein the position information is information based on a three-dimensional shape of the hand shown at the opening portion, and the light amount control portion controls the light amount of the irradiation light source in accordance with a length of a distance from the irradiation light source to the hand irradiated by the irradiation light source.

4. The blood-vessel image capturing apparatus according to claim 3, wherein the blood-vessel image capturing apparatus calculates, on a basis of information obtained from the sensor, a center position of the hand and a direction of the finger portion with respect to the center position in an image of a region of the hand included in the image, and calculates a rotation angle of the hand.

5. The blood-vessel image capturing apparatus according to claim 4, wherein the plural light sources are disposed at positions out of a detection range of the sensor and an image capturing range of the image capturing portion.

6. The blood-vessel image capturing apparatus according to claim 5, wherein a wavelength of light radiated from the sensor is different from a wavelength of light radiated from the plural light sources.

7. The blood-vessel image capturing apparatus according to claim 6, wherein the sensor is disposed at such a position that a distance from the sensor to a center of the opening portion is longer than a distance from the plural light sources to the center of the opening portion.

8. The blood-vessel image capturing apparatus according to claim 7, wherein the light amount control portion selects the light source disposed further on a moving direction side than the hand with respect to the moving direction of the hand moving above the opening portion as the irradiation light source.

9. The blood-vessel image capturing apparatus according to claim 8, further comprising, on the surface of the housing, a reading portion configured to receive personal information from a terminal attachable to a wrist.

10. The blood-vessel image capturing apparatus according to claim 9, wherein the blood-vessel image capturing apparatus transmits the image to an authentication portion that executes authentication of an individual.

11. An individual authentication system comprising:
a terminal including an opening portion formed in a surface of a housing, plural light sources disposed beside the opening portion and arranged in a lattice pattern, a sensor configured to obtain position information of a hand shown above the opening portion, a light amount control portion configured to select an irradiation light source to irradiate the hand from the plural light sources on a basis of the position information and control a light amount of the irradiation light source, and an image capturing portion configured to capture an image of a blood vessel included in a finger portion of the hand irradiated with light from the irradiation light source;
an authentication portion configured to obtain the image from the terminal and execute authentication of an individual; and
a gate portion configured to open and close on a basis of information from the authentication portion;
wherein the light amount control portion selects a light source that irradiates a root side of the finger portion as the irradiation light source from the plural light sources on the basis of the position information; and
wherein, among the plural light sources, an acute angle made by an opening plane of the opening portion and an optical axis of a light source is smaller for the light source positioned from the opening portion by a smaller distance than the other light sources.

12. The individual authentication system according to claim 11, wherein a wavelength of light radiated from the sensor is different from a wavelength of light radiated from the plural light sources.

* * * * *